(12) United States Patent
Bergeron et al.

(10) Patent No.: US 7,357,930 B1
(45) Date of Patent: Apr. 15, 2008

(54) METHODS AND FORMULATIONS FOR TARGETING INFECTIOUS AGENTS BEARING HOST CELL PROTEINS

(75) Inventors: Michel G. Bergeron, Quebec (CA); Andre Desormeaux, Neufchatel (CA); Michel J. Tremblay, Neufchatel (CA)

(73) Assignee: Infectio Recherche Inc., Quebec (CA)

( * ) Notice: Subject to any disclaimer, the term of this patent is extended or adjusted under 35 U.S.C. 154(b) by 0 days.

(21) Appl. No.: 09/980,516

(22) PCT Filed: May 3, 2000

(86) PCT No.: PCT/CA00/00469

§ 371 (c)(1),
(2), (4) Date: Apr. 3, 2002

(87) PCT Pub. No.: WO00/66173

PCT Pub. Date: Nov. 9, 2000

(30) Foreign Application Priority Data

May 3, 1999 (CA) .................................... 2270600

(51) Int. Cl.
*A61K 9/127* (2006.01)
*A61K 39/00* (2006.01)
*A61K 31/7115* (2006.01)
*A61K 31/712* (2006.01)

(52) U.S. Cl. ..................... 424/178.1; 424/450; 514/45; 514/49; 514/50; 514/934

(58) Field of Classification Search ................ 424/450, 424/9.321, 9.34, 9.51, 178.1; 514/394, 934, 514/45, 49, 50
See application file for complete search history.

(56) References Cited

U.S. PATENT DOCUMENTS

| 5,013,556 A | 5/1991 | Woodle et al. |
| 5,773,027 A * | 6/1998 | Bergeron et al. |

FOREIGN PATENT DOCUMENTS

| BR | 9509217 | 1/1998 |
| EP | 0196185 A2 | 10/1986 |
| EP | 0 286 418 A1 | 12/1988 |
| NO | 971494 | 5/1997 |
| WO | 8701283 A1 | 3/1987 |
| WO | 8701284 A1 | 3/1987 |
| WO | 96/10399 | 4/1996 |
| WO | 96/10399 A1 | 4/1996 |
| WO | 96/10585 | 4/1996 |
| WO | 96/25147 | 8/1996 |

OTHER PUBLICATIONS

Harlow et al, in Antibodies a Laboratory Manual, 1988, Cold Spring harbor laboratory publication, Cold Spring Harbor, NY, pp. 626-629.*
Selvam et al, Antivrial Research 33: 11-20, 1996.*
Desormeaux A. et al.: "Targeting HIV with liposome encapsulated antivirals" ZBL. BAKT., vol. 282, Apr. 1995 ppp. 225-231.
Phillips N.C.: "Immunoliposome targeting to murine CD4+ leucocytes is dependent on immune status" J. Immunol., vol. 152, 1994, pp. 3168-3174.
Desormeaux A. et al.: "Liposomes as drug delivery system: a strategic approach for the treatment of HIV infection" J Drug Targeting, vol. 6, No. 1, 1998, pp. 1-15.
Maruyama K. et al.: "Possibility of active targeting to tumor tissues with liposomes" Adv Drug Deliv Reviews, vol. 40, Oct. 10, 1999, pp. 89-102.
Menezes De D E L et al.: "Cellular Trafficking and Cytotoxicity of Anti-CD19-Targeted Liposomal Doxorubicin In B Lymphoma Cells" Journal of Liposome Research, US, Marcel Dekker, New York, vol. 9, No. 2, May 1999, pp. 199-228.
Lundberg B. B. et al.: "Specific binding of sterically stabilized anti-B-cell immunoliposomes and cytotoxicity of entrapped doxorubicin" Int J Pharmac, vol. 205, Sep. 2000, pp. 101-108.
Bestman-Smith J. et al.: "Sterically stabilized liposomes bearing anti-HLA-DR antibodies for targeting the primary cellular reservoirs of HIV-1" Biochim Biophys Acta, vol. 1468, Sep. 29, 2000, pp. 161-174.
Bestman-Smith J. et al.: "Targeting cell-free HIV and virally infected cells with anti HLA-DR immunoliposomes containing amphotericin B" AIDS, vol. 14, Oct. 10, 2000, pp. 2457-2465.
Dufresne I. et al.: "Targeting lymph nodes with liposomes bearing anti-HLA-DR Fab' fragments" Biochim Biophys Acta, vol. 1421, Oct. 15, 1999, pp. 284-294.

(Continued)

*Primary Examiner*—Christina Chan
*Assistant Examiner*—Phuong Huynh
(74) *Attorney, Agent, or Firm*—Whyte Hischboeck Dudek SC

(57) ABSTRACT

A formulation is disclosed for the treatment of diseases caused by an infectious agent which acquires host membranes protein during its life cycle. The formulation is a targeting pharmaceutical composition. It comprises a ligand capable of binding the host membrane proteins coupled to a lipid-comprising vesicle, which may comprise or not a drug effective in the treatment of the disease. Specific liposomes bearing anti-HLA-DR or anti-CD4 antibodies comprising or not antiviral drugs, namely anti-HIV drugs, are disclosed and claimed. A method of formulation as well as a method of using the formulation in the treatment of a disease are also disclosed.

16 Claims, 15 Drawing Sheets

OTHER PUBLICATIONS

Zelphati et al.: "Inhibition of HIV-1 Replication in Cultured Cells with Antisense Oligonucleotides Encapsulated in Immunoliposomes" Antisense Research and Development, vol. 3, 1993, pp. 323-338.

Chun, T.-W. et al. (1998). "Early establishment of a pool of latently infected, resting CD4+ T cells during primary HIV-1 infection". Proc. Natl. Acad. Sci. USA. vol. 95: 8869-8873.

Cantin, R. et al. (1997) "The Presence of Host-Derived HLA-DR1 on Human Immunodeficiency Virus Type 1 Increases Viral Infectivity", Journal of Virology, vol. 71(3): 1922-1930.

Finzi, D. et al. (1997). "Identification of a Reservoir for HIV-1 in Patients on Highly Active Antiretroviral Therapy". Science, vol. 278: 1295-1300.

Finzi, D. et al. (1999). "Latent infection of CD4+ T cells provides a mechanism for lifelong persistence of HIV-1, even in patients on effective combination therapy". Nature Medicine, vol. 5(5):512-517.

Saarloos, M.-N. et al. (1997). "Detection of HLA-DR Associated with Monocytotropic, Primary, and Plasma Isolates of Human Immunodeficiency Virus Type 1". Journal of Virology, vol. 71(2): 1640-1643.

Tremblay, M. J. et al. (1998). "The acquisition of host-encoded proteins by nascent HIV-1". Immunology Today, vol. 19(8): 346-351.

Knox, Pauline G. et al., Epstein-Barr Virus Infection of CR2-Transfected Epithelial Cells Reveals the Presence of MHC Class II on the Virion, Virology 21, 147-157 (1995).

Saifuddin, Mohammed et al., Transfer of Host T-Cell Membrane HLA-DR and CD25 to Target Cells by Human Retroviruses, Journal of Acquired Immune Deficiency Syndromes and Human Retrovirology, 17:196-202, 1998.

Arthur, Larry O., et al., Cellular Proteins Bound to Immunodeficiency Viruses: Implications for Pathogenesis and Vaccines, Science, vol. 258, 1935-1938, Dec. 18, 1992.

Norley SG et al., J. Immunol., 1986, pp. 681-685, vol. 136(2).

Norley et al., Chemical Abstracts, 1986, pp. 391-30=92, vol. 104(14).

Furmanski et al., Cancer Lett., 1980, pp. 307-317, vol. 8(4).

Furmanski et al., Chemical Abstracts, 1980, p. 49, vol. 92(21).

Mayhew et al., Cancer Res., 1976, pp. 4406-4411, vol. 36(12).

Mayhew et al., Chemical Abstracts, 1977, pp. 28-29, vol. 86(9).

* cited by examiner

FIG_2

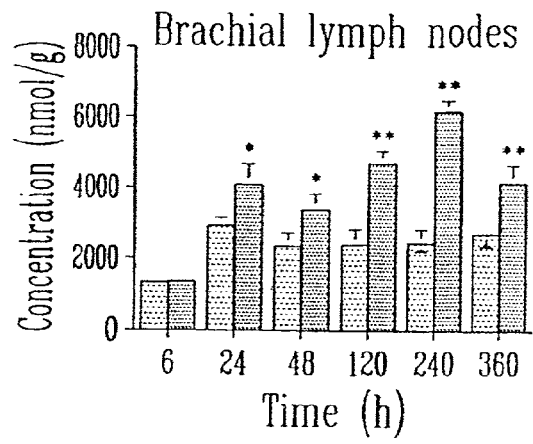
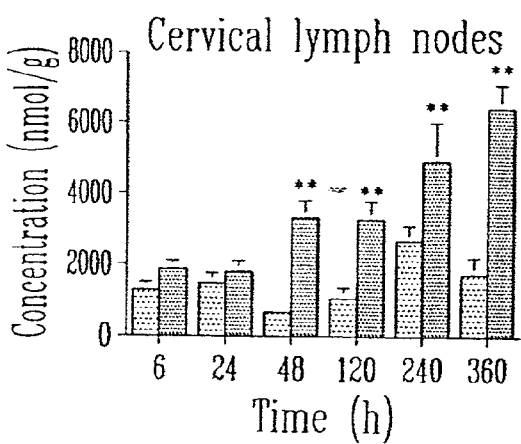
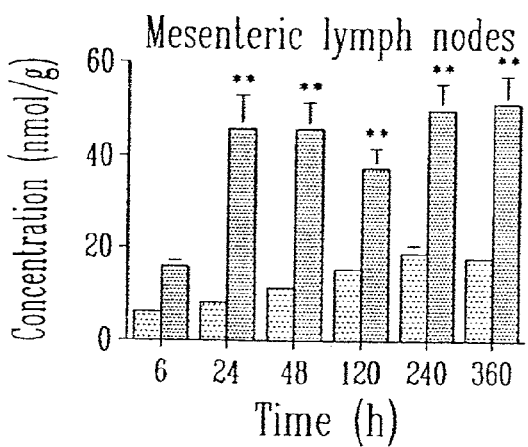
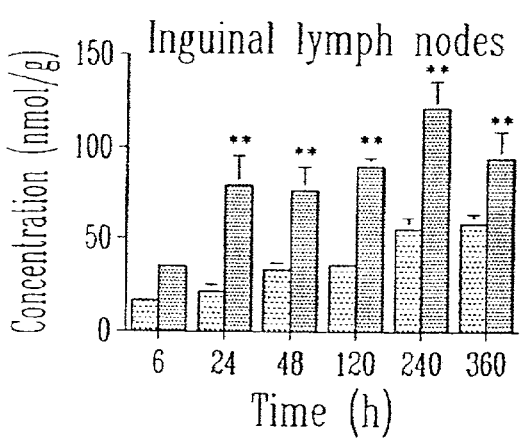
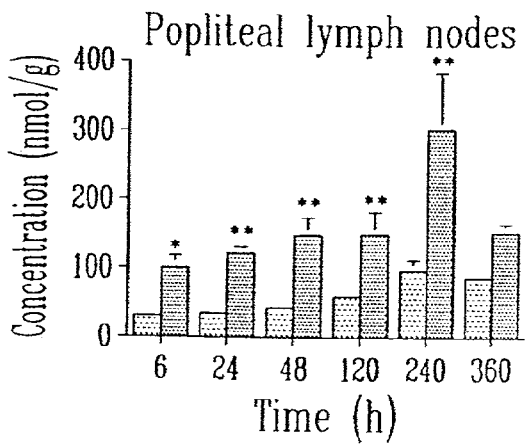
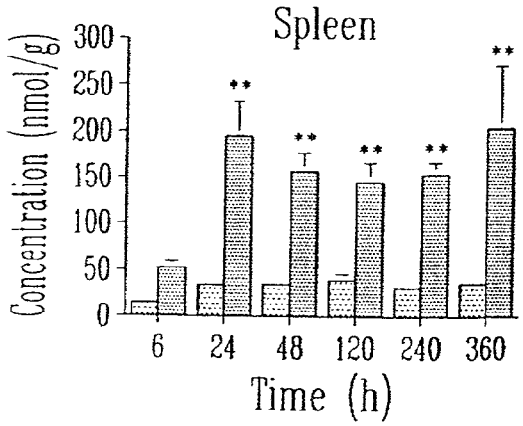
FIG_4

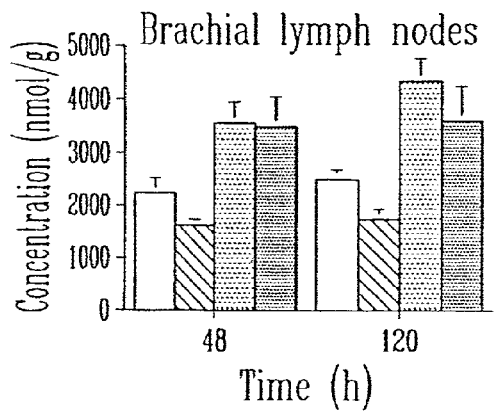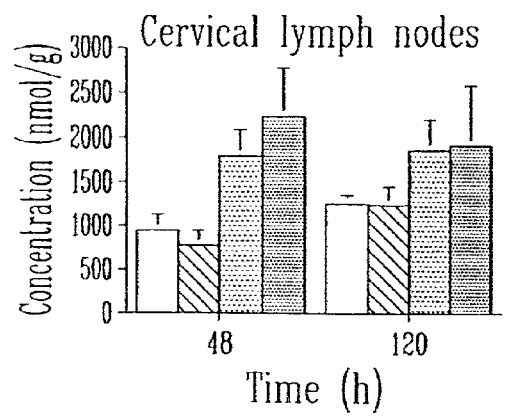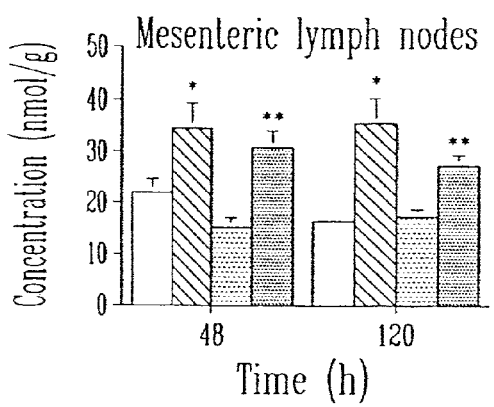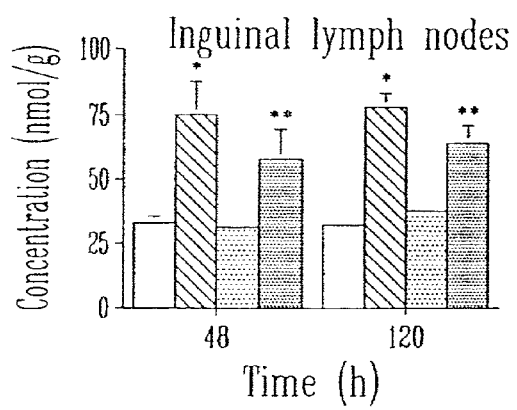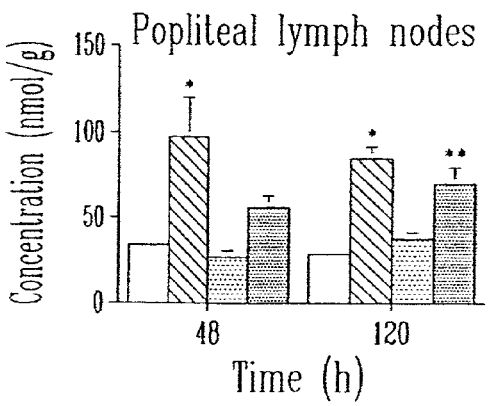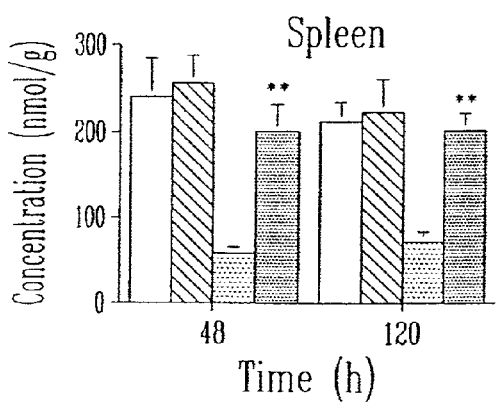
FIG. 5

METHODS AND FORMULATIONS FOR TARGETING INFECTIOUS AGENTS BEARING HOST CELL PROTEINS

CROSS-REFERENCE TO RELATED APPLICATIONS

This application claims priority to International Application No. PCT/CA00/00469, filed May 3, 2000 (Publ. No. WO0066173), and Canadian Application No. 2,270,600, filed May 3, 1999.

FIELD OF THE INVENTION

This invention relates to formulations of ligands capable of binding to host membrane proteins present at the membrane surface of infectious agents as well as at the membrane surface of the host cells. More specifically, this invention relates to ligand-conjugated vesicles that may be administered alone or in combination with a drug. The drug may be incorporated into the vesicles or administered concurrently. Even more specifically, the protein is HLA-DR or CD4, the ligand is an anti-HLA-DR or anti-CD4 antibody or antibody fragment and the vesicles are liposomes. The drugs are preferably directed to a disease caused by HIV. These formulations could be used either as a therapeutic or a preventive tool.

BACKGROUND OF THE INVENTION

It is now well-established that in the early-stage of human immunodeficiency virus (HIV) infection and throughout the clinical latent stage, viral particles accumulate and replicate actively in lymphoid organs despite a low viral load in peripheral blood. The high viral load observed in the lymphoid tissues was reported to be partly associated with trapped HIV particles on the follicular dendritic cells (FDC) located in the germinal centers. In addition to the extracellular localization of HIV in interdendritic spaces of germinal centers, viral particles are also found within the endosomal and cytoplasm compartments of FDC. Moreover, viral particles bound to the FDC remained highly infectious to CD4+ T-cells despite the presence of neutralizing antibodies on their surface. Over the course of HIV infection, the FDC network was shown to be gradually disrupted and ultimately destroyed. The incapacity of FDC to retain HIV particles in advanced stages of the disease has been postulated to contribute to the increased viral burden in the periphery. As the microenvironment of lymphoid tissues is crucial for effective immune responses, it is important to reduce or abrogate the production and the accumulation of HIV-1 particles in these tissues to preserve both their architecture and integrity.

Highly active antiretroviral therapy (HAART), usually consisting in the combination of two nucleoside analogues and one protease inhibitor, has been shown to be effective to reduce the plasma viral load to undetectable levels in HIV-infected individuals. However, anti-HIV regimens do not fully eliminate viral replication in secondary lymphoid tissues and this continued replication of HIV-1 seems to be due to the presence of drug-sensitive viruses. In addition, replication-competent HIV-1 are routinely isolated from resting CD4+ T-cells from patients receiving HAART even after 30 months of therapy (Finzi et al., 1997, Science, 278:1295-1300). In fact, it was estimated that it would take as much as 60 years to eradicate HIV from an infected individual (Finzi et al., 1999, Nature Med. 5:609-611). In addition, it was shown that initiation of HAART in HIV-infected patients, as early as 10 days after the onset of symptoms of primary HIV-1 infection, did not prevent generation of latently infected resting CD4+ T-cells carrying integrated HIV-1 DNA despite the successful control of plasma viremia (Chun et al., 1998; Proc. Natl. Acad. Sci. USA 95:8869-8873). On the other hand, an increasing number of treatment failures resulting from toxicity, drug-resistant mutants and/or poor compliance of patients to drug regimen are emerging with long-term therapy.

All approved anti-HIV drugs are generally aimed at blocking viral replication within cells by inhibiting either HIV-1 reverse transcriptase or protease which are essential enzymes for viral replication. Antiviral drugs include anti-HIV drugs such as 3'-azido-3'-deoxythymidine (AZT, zidovudine), 2'-3'-dideoxyinosine (ddI; didanosine), 2'-3'-dideoxycytidine (ddC; zalcitabine), 2'-deoxy-3'-thiacytidine (3TC; lamivudine), indinavir, saquinavir, ritonavir, nelfinavir, ganciclovir, foscarnet and ribavirin. The development of new drugs that targets other events of HIV-1 infection or the use of alternative approaches for the treatment of HIV-1 infection remains a high priority to cure this deadly disease. Most polyene macrolide antibiotics are active against a variety of lipid-enveloped RNA and DNA viruses. The binding of these drugs to sterols located within microbial cell membranes modifies the permeability and function of cells decreasing the infectivity of lipid-enveloped virus. Both amphotericin B (AmB) and nystatin A have been shown to be efficient to inhibit the in vitro replication of HIV-1, probably via the binding of drugs to cholesterol in the membrane of HIV-1, which has a high cholesterol-to-phospholipid ratio. Antiviral activity of a series of more soluble derivatives of AmB has also been investigated. The mechanism of action by which these molecules inhibit HIV-1 infection was shown to be markedly different upon the nature of the AmB derivative, their main target being the viral and/or cellular membrane.

One common feature of retroviruses, as well as of many other enveloped viruses, is the acquisition of host cell surface molecules during the budding process. FDC, B lymphocytes, antigen presenting cells like macrophages and activated CD4+ T-cells are abundant in lymphoid tissues and all express substantial levels of the HLA-DR determinant of the major histocompatibility complex class II (MHC-II). Monocyte-derived macrophages, which are also CD4+ and express HLA-DR, are considered to be the most frequently identified hosts of HIV-1 in tissues of infected individuals. Given that HIV-1 has been reported to incorporate a vast array of cell membrane derived structures while budding out of the infected cell, the probability that newly formed viral entities will bear cellular HLA-DR is thus high. It has been demonstrated that plasma HIV-1 isolates from virally-infected individuals do carry on their surface host-encoded HLA-DR (Saarioos et al., 1997, J. Virol. 71:1640-1643). The physiological relevance of cellular HLA-DR bound to HIV-1 is further provided by previous studies from our laboratory indicating that HLA-DR is one of the most abundant host-derived molecules carried by HIV-1 (Cantin et al., 1997, J. Virol. 71:1922-1930). Numerous reports have provided evidence for the presence of many other host-derived components in different laboratory and/or primary isolates of HIV-1 (Table 1; for review see Tremblay et al., 1998, Immunol. Today 19:346-351).

There is serious doubt about the ability of current antiviral treatment to eradicate HIV-1 infection. Therefore, more potent antiretroviral drugs or the use of alternative approaches that block the potential spread of virus within lymphoid tissues, their main reservoir, are urgently needed. Considering that HIV accumulates and replicates actively within lymphoid tissues, any strategy that will decrease viral stores in these tissues might be beneficial to the infected host. As liposomes are naturally taken up by cells of the mononuclear phagocytic system (MPS), liposome-based therapy represents a convenient approach to improve the delivery of anti-HIV agents within lymphoid tissues. As host-derived HLA-DR proteins are abundantly expressed on antigen presenting cells such as monocyte/macrophages and FDC, liposomes bearing surface-attached anti-HLA-DR antibodies (anti-HLA-DR immunoliposomes) and containing anti-HIV agents constitute a convenient approach to target even more specifically HIV-1 reservoirs. Similarly, the coupling of anti-CD4 molecules on the surface of liposomes (anti-CD4 immunoliposomes) should lead to a specific targeting of both CD4 T-lymphocytes and monocyte/macrophages which represent the major cellular reservoir for HIV-1. Furthermore, as host-encoded HLA-DR determinant is also present on the virion's surface, incorporation of neutralizing agents, such as amphotericin B, in anti-HLA-DR immunoliposomes represents an attractive strategy to destroy cell-free viruses. Taken together, the use of immunoliposomal drugs represents an attractive strategy to target primary cellular reservoirs of HIV-1. Such a targeted drug delivery system could hopefully improve the treatment of HIV infection.

U.S. Pat. No. 5,773,027 discloses the use of antiviral agents encapsulated into liposomes for the treatment of viral diseases. However, this publication does not specifically teach liposomes bearing surface-attached antibodies comprising or not a drug capable of inhibiting replication or destroying both cell-free HIV virions and virally-infected cells. Such immunoliposomes could represent a novel therapeutic strategy to treat more efficiently this retroviral disease.

TABLE 1

Host proteins acquired by HIV-1

| Host protein (other name) | Producer cell (cellular origin)[a] | Strain of HIV-1 (source)[b] |
|---|---|---|
| CD3 (T3) | H9 (T) | IIIB (L) |
| CD4 (T4) | PBMCs, H9 (T) | IIIB (L) |
| CD5 (T1) | PBMCs, H9 (T) | IIIB (L) |
| CD6 (T12) | PBMCs, H9 (T) | IIIB (L) |
| CD8 (T8) | Sup-T1 (T) | IIIRF (L) |
| CD11a (LFA-1) | PBMCs, H9 (T), Sup-T1 (T), CEMx174 (T), Jurkat (T), CEM.NK[r] (T), C8166 (T), U937 (M), AA2 (B) | IIIB (L), IIIRF (L), P1 (P) |
| CD11b (Mac-1) | H9 (T), U937 (M) | IIIB (L) |
| CD11c (gp 150,95) | H9 (T), U937 (M), AA2 (B) | IIIB (L) |
| CD15 (Lewis-X) | U937 (M) | IIIB (L) |
| CD18 | PBMCs, H9 (T), Sup-T1 (T), Jurkat (T), CEMx174 (T), CEM.NK[r] (T), C8166 (T) U937 (M), AA2 (B) | IIIRF (L), IIIB (L), P1 (P) |
| CD19 | AA2 (B) | IIIB (L) |
| CD25 (Tac) | PBMCs, H9 (T) | IIIB (L) |
| CD30 (Ki-1) | H9 (T) | IIIB (L) |
| CD43 (leukosialin, sialophorin) | PBMCs, CEMx174 (T), Jurkat (T), CEM.NK[r] (T), Sup-T1 (T), H9 (T), U937 (M), AA2 (B) | IIIRF (L), IIIB (L) |
| CD44 (Pgp-1) | CEMx174 (T), Sup-T1 (T), CEM.NK[r] (T) | IIIRF (L) |
| CD48 (Blast-1) | PBMCs, H9 (T), U937 (M) | IIIB (L) |
| CD54 (ICAM-1) | PBMCs, H9 (T), C8166 (T), U937 (M), AA2 (B), RAJI-CD4 (B) | IIIB (L), IIIRF (L), LAI (L), NL4-3 (L), P1(P), 334 (P), 336 (P), 438 (P) |
| CD55 (DAF) | PBMCs, H9 (T), U937 (M), AA2 (B) | NL4-3 (L), IIIB (L), JC50 (P), MG 47 (P), MP49 (P), PE51 (P), CJ48 (P) |
| CD59 (Protectin, Mac inhibitor) | PBMCs, H9 (T), U937 (M), AA2 (B) | NL4-3 (L), IIIB (L), JC50 (P), MG 47 (P), MP49 (P), PE51 (P), CJ48 (P) |
| CD63 | PBMCs, H9 (T), Jurkat (T), Sup-T1 (T), CEMx174 (T), CEM.NK[r] (T) | IIIB (L), IIIRF (L) |
| CD71 (Transferrin receptor) | PBMCs, CEMx174 (T), Sup-T1 (T), H9 (T), U937 (M), AA2 (B) | IIIRF (L), IIIB (L) |
| CDw108 (GR2) | H9 (T), U937 (M), AA2 (B) | IIIB (L) |
| Cyctophilin A | $CEM_{ss}$ (T), HeLa (E), COS (F) | NL4-3 (L), HXB2 (L) HXBH10 (L), IIIMN (L) |
| Cytosketetal proteins | H9 clone 4 (T), $CEM_{ss}$ (T) | IIIMN (L) |
| HLA-DP, -DQ | PBMCs, RAJI-CD4 (B) | LAI (L), IIIRF (L), NL4-3 (L), 334 (P), 336 (P), 438 (P) |

TABLE 1-continued

Abbreviations: HIV-1: human immunodeficiency virus type 1; HLA-DP and DQ, human leukocyte antigen loci DP and DQ; PBMCs, peripheral blood mononuclear cells.

[a]Cellular origin: B, B-lymphoblastic; E, epithelial-like; F, fibroblast-like; M, monocytic; T, T lymphoblastoid. [b]Source: L, laboratory isolates of HIV-1; P, primary isolates of HIV-1.

SUMMARY OF THE INVENTION

This invention provides new formulations having the capacity of targeting an infectious agent, which has acquired at least one host membrane protein during its life cycle in its free form, as well as targeting the host cell itself.

This invention provides formulations which comprise ligand-conjugated vesicles that may be administered alone or in combination with a drug, for the purpose of treating or for alleviating the symptoms of a disease caused by the infectious agent. Furthermore, the ligand-conjugated vesicles could be incorporated in a gel or any other carrier to prevent or treat any disease of mucosae and/or skin. These formulations could also be used as carriers of passive vaccines against infections caused by pathogens or any disease. The drug may be incorporated into the vesicles or administered concurrently.

In a specific embodiment, the host cell is a lymphoid cell or a cell of the reticuloendothelial system. In still a more preferred version of this invention, the infectious agent is HIV. It is however clear that this invention can be applicable to any host cell infected by any infectious agent which has a life cycle such that host membrane proteins are acquired during the budding process or the construction of its external constituents. For example, a liver cell susceptible to a hepatitis virus, or a mucosal epithelial cell susceptible to a herpes virus, are versions considered within the scope of this invention.

The targeted host membrane protein is any one which is expressed by the whole cell, and acquired by the infectious agent. This protein may be selected from a histocompatibility complex protein, a membrane ATPase, thy-1, an interleukin receptor, annexin II, $\beta_2$-microglobulin, CD3 (T3), CD4 (T4), CD5 (T1), CD6 (T12), CD8 (T8), CD11a (LFA-1), CD11b (Mac-1), CD11c (gp150,95), CD1 (Lewis X), CD18, CD19, CD25 (Tac), CD30 (Ki-1), CD43 (leukosialin, sialophorin), CD44 (Pgp-1), CD48 (Blast-1), CD54 (ICAM-1), CD55 (DAF), CD59 (protectin, Mac inhibitor), CD63, CD71 (transferrin receptor), CDw108 (GR2), cyclophilin A, and cytoskeletal proteins. The first contemplated protein candidates are those that are involved in the increased infectivity of HIV, namely HLA-DR, MHC-I and CD54.

In one version of this invention, the formulation comprises a ligand coupled to a lipid-comprising vesicle. In another version of this invention, the formulation comprises a ligand-conjugated vesicle containing a drug incorporated into the vesicles. The lipid-comprising vesicle includes nanoerythrosomes or liposomes.

The ligand may be selected from a surface antigen, an agonist, an antagonist, and an antibody molecule. In a preferred version of this invention, the ligand is an antibody molecule which is selected from a whole antibody and an antibody fragment capable of binding the protein of interest.

Also in a preferred version of this invention, the vesicle comprises a liposome, a sterically stabilized liposome (stealth liposome), and a combination thereof. The coupling of these liposome forms with an antibody molecule thus provides immunoliposomes.

The formulation may also comprise, besides immunoliposomes, conventional liposomes (sterically stabilized or not), comprising an effective amount of entrapped drug.

The drug contemplated in this invention is capable of affecting the cell, via its coupling with the ligand, and its binding to a cell membrane protein, for the purpose of targeting the cell of interest. The drug can also be effective directly against the free infectious agent. In so far AIDS is the disease to be treated, the drug may be selected from AZT, ddI, ddC, 3TC, indinavir, saquinavir, ritonavir, nelfinavir, ganciclovir, foscarnet, ribavirin, amphotericin B and nystatin A.

In the most specific version of this invention, the formulation is an immunoliposome coupled to an anti-HLA-DR or anti-CD4 antibody Fab' fragment and comprising indinavir or amphotericin B as an entrapped antiviral drug.

Liposomes of the present invention are composed of any vesicle-forming lipid. For the purpose of this invention, the term "vesicle-forming lipid" is intended to cover any amphipathic lipid having hydrophobic and polar head group moieties which can form bilayer vesicles in aqueous solutions or can be incorporated into lipid bilayers. Included in this class are phospholipids such as phosphatidylcholine (PC), phosphatidylglycerol (PG), phosphatidylethanolamine (PE), phosphatidylserine (PS), phosphatidylinositol (PI), phosphatidic acid (PA) and sphingomyelin (SM) where the two hydrocarbon chains are typically between about 14-22 carbon atoms in length and have varying degrees of unsaturation. Also included in this class are glycolipids, such as cerebrosides and gangliosides. Also included in this class are cholesterol and related sterols. Also included in this class are amphipathic lipids having a derivatized hydrophilic biocompatible polymer such as polyethyleneglycol (PEG). The PEG preferably has a molecular weight ranging from about 500 to 5000 daltons. The lipid-PEG derivative is present in a proportion of about 0.75-20%, preferably about 2.5-10%. The liposomes of the present invention are most preferably composed of i) a mixture of diacylphosphatidylcholine and diacylphosphatidylglycerol (in a molar ratio ranging between 10:1 and 1:1) wherein the acyl chains are either saturated or unsaturated and have between 14 and 18 carbon atoms in length. The liposomes of the present invention also include immunoliposomes, defined herein as, liposomes which are modified by the coupling of antibody molecules which enhance the targeting of specific cells. The liposomes of the present invention also include pH-sensitive liposomes, heat-sensitive liposomes, target-sensitive liposomes and any other type of liposomes that could be used for this purpose. This invention also covers any combination of liposomes and/or drugs.

The preferred formulations of liposomes comprise dipalmitoylphosphatidylcholine (DPPC):dipalmitoylphosphatidylglycerol (DPPG) in a molar ratio of 10:3 (thereafter illustrative of conventional liposomes). In another embodiment, formulations of liposomes comprise diacylphosphatidylcholine:diacylphosphatidylglycerol in a molar ratio of about 10:3. In another embodiment, formulations of liposomes comprise a mixture of diacylphosphatidylcholine:diacylphosphatidylglycerol:diacylphosphatidylethanolamine-polyethyleneglycol in a molar ratio of 10:3:0.1-3. In another embodiment, formulations of liposomes comprise a mixture of dipalmitoylphosphatidylcholine:dipalmitoylphosphatidylglycerol in a molar ratio of 10:3 or distearoylphosphatidylcholine:distearoylphosphatidylglycerol in a molar ratio of 10:3. In another preferred embodiment, formulations of liposomes comprise DPPC:DPPG:distearoylphosphatidylethanolamine-polyethyleneglycol (DSPE-PEG) in a molar ratio of 10:3:0.83 (thereafter illustrative of sterically stabilized liposomes or stealth liposomes). In another embodiment, formulations of liposomes comprise a mixture of dipalmitoylphosphatidylcholine:dipalmitoylphosphatidylglycerol:dipalmitoylphosphatidylethanolamine-polyethyleneglycol in a molar ratio of 10:3: 0.33 or dipalmitoylphosphatidylcholine:dipalmitoylphosphatidylglycerol:distearoylphosphatidylethanolamine-polyethyleneglycol in a molar ratio of 10:3:0.83. In still another preferred embodiment, formulations of liposomes comprise DPPC:DPPG:dipalmitoylphosphatidylethanolamine-N-(4-(p-maleimidophenyl)butyryl)(DPPE-MPB) in a molar ratio of 10:3: 0.33 bearing anti-HLA-DR Fab' fragments (thereafter illustrative of anti-HLA-DR immunoliposomes). In still another preferred embodiment, formulations of liposomes comprise DPPC:DPPG:DPPE-MPB in a molar ratio of 10:3: 0.33 bearing anti-CD4 Fab' fragments (thereafter illustrative of anti-CD4 immunoliposomes). In still another preferred embodiment, formulations of liposomes comprise DPPC: DPPG:DSPE-polyethyleneglycol-MPB (DSPE-PEG-MPB) in a molar ratio of 10:3:0.83 bearing anti-HLA-DR Fab' fragments (thereafter illustrative of sterically stabilized anti-HLA-DR immunoliposomes or stealth anti-HLA-DR immunoliposomes). In still another preferred embodiment, formulations of liposomes comprise DPPC:DPPG:DSPE-PEG-MPB in a molar ratio of 10:3:0.83 bearing anti-CD4 Fab' fragments (thereafter illustrative of sterically stabilized anti-CD4 immunoliposomes or stealth anti-CD4 immunoliposomes). MPB is a coupling agent that may be replaced with any other suitable molecule for the purpose of attaching a ligand to a lipid or lipid derivative.

Other preferred formulations of liposomes comprise DPPC:DPPG in a molar ratio of 10:3 and contains amphotericin B as an antiviral drug. In still another preferred embodiment, formulations of liposomes comprise DPPC: DPPG in a molar ratio of 10:3 and contains indinavir as an antiviral drug. In still another preferred embodiment, formulations of liposomes comprise DPPC:DPPG:DSPE-PEG in a molar ratio of 10:3:0.83 and contains amphotericin B as an antiviral drug. In still another preferred embodiment, formulations of liposomes comprise DPPC:DPPG:DSPE-PEG in a molar ratio of 10:3:0.83 and contains indinavir as an antiviral drug. In still another preferred embodiment, formulations of liposomes comprise DPPC:DPPG-DPPE-MPB in a molar ratio of 10:3:0.33 bearing anti-HLA-DR Fab' fragments and contains amphotericin B as an antiviral drug. In still another preferred embodiment, formulations of liposomes comprise DPPC:DPPG-DPPE-MPB in a molar ratio of 10:3:0.33 bearing anti-HLA-DR Fab' fragments and contains indinavir as an antiviral drug. In still another preferred embodiment, formulations of liposomes comprise DPPC:DPPG-DPPE-MPB in a molar ratio of 10:3:0.33 bearing anti-CD4 Fab' fragments and contains amphotericin B as an antiviral drug. In still another preferred embodiment, formulations of liposomes comprise DPPC:DPPG-DPPE-MPB in a molar ratio of 10:3:0.33 bearing anti-CD4 Fab' fragments and contains indinavir as an antiviral drug. In still another preferred embodiment, formulations of liposomes comprise DPPC:DPPG:DSPE-PEG-MPB in a molar ratio of 10:3:0.83 bearing anti-HLA-DR Fab' fragments and contains amphotericin B as an antiviral drug. In still another preferred embodiment, formulations of liposomes comprise DPPC:DPPG:DSPE-PEG-MPB in a molar ratio of 10:3:0.83 bearing anti-HLA-DR Fab' fragments and contains indinavir as an antiviral drug. In still another preferred embodiment, formulations of liposomes comprise DPPC:DPPG:DSPE-PEG-MPB in a molar ratio of 10:3:0.83 bearing anti-CD4 Fab' fragments and contains amphotericin B as an antiviral drug. In still another preferred embodiment, formulations of liposomes comprise DPPC:DPPG:DSPE-PEG-MPB in a molar ratio of 10:3:0.83 bearing anti-CD4 Fab' fragments and contains indinavir as an antiviral drug.

DETAILED DESCRIPTION OF THE INVENTION

The present invention is described herein below by way of specific examples and appended figures, whose purpose is to illustrate the invention rather than to limit its scope.

BRIEF DESCRIPTION OF THE FIGURES

FIG. 4 shows the tissue distribution of conventional immunoliposomes (dotted bar) and sterically stabilized anti-HLA-DR immunoliposomes (solid bar) in brachial, cervical, mesenteric, inguinal and popliteal lymph nodes, and spleen following a single subcutaneous injection to mice. Values represent mean (±SEM) obtained for six animals per group per time point. *, **Significantly different (p<0.05) and (p<0.01), respectively when compared to conventional immunoliposomes.

FIG. 5 shows the tissue distribution of conventional liposomes (empty bar), sterically stabilized liposomes (lined bar), conventional anti-HLA-DR immunoliposomes (dotted bar) and sterically stabilized anti-HLA-DR immunoliposomes (solid bar) in brachial, cervical, mesenteric, inguinal and popliteal lymph nodes, and spleen following a single subcutaneous injection to mice. Values represent the mean (±SEM) obtained for six animals per group per time point. *Significantly different (p<0.05) when compared to conventional liposomes and **significantly different (p<0.05) when compared to conventional anti-HLA-DR immunoliposomes.

DESCRIPTION OF THE SPECIFIC EMBODIMENTS OF THE INVENTION

Drugs

Figure 1:
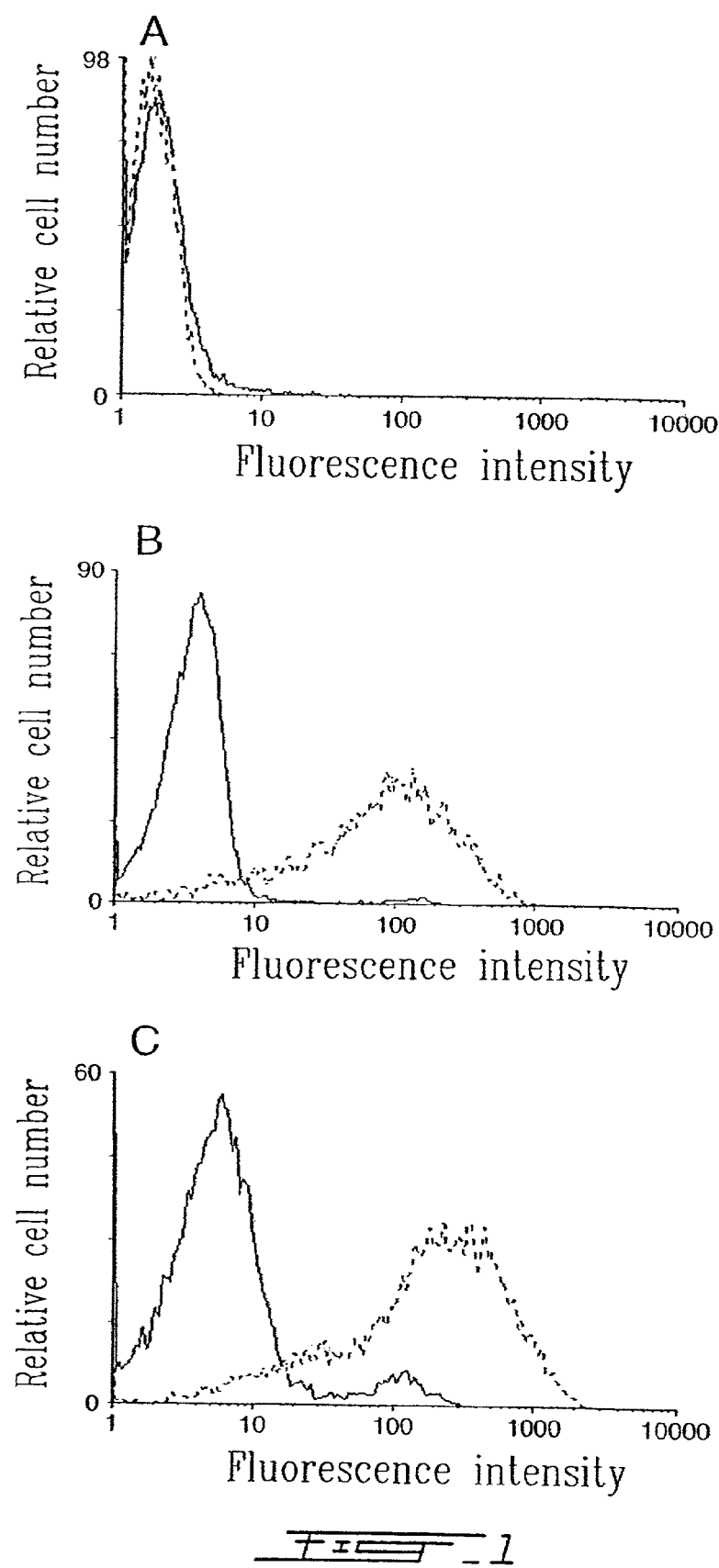
FIG. 1 shows flow cytometry scans of A) SUP-T1, B) HUT-78 and C) RAJI cells incubated with conventional liposomes (solid lines) and anti-HLA-DR immunoliposomes (dotted lines) for 30 min at 37° C. and revealed with a goat-anti-mouse-FITC-IgG.

Any antimicrobial, bactericidal, virucidal, chemotherapeutic, antiinflammatory, antineoplastic, immunomodulator or any other agent or combination of them which is effective to treat infection and/or disease is under the scope of this invention. The term "drug" also refers to cytokines or antigens that could stimulate an immune response that would lead to an improved treatment against the said infection and/or disease.

Liposomes

The preparation of liposomes in the present invention can be carried out by a variety of techniques such as those described in the literature. Formulations of liposomes of the present invention include those having a mean particle diameter of any size prepared with any drug/lipid molar ratio. Incorporation of drugs into liposomes can be achieved by one or more methods of active and/or passive loading such as those described in the literature. Details for the preparation of liposomes are provided in the following examples.

Examples Involving our Liposomal Formulations for Treatment of Infection

The following examples are intended to demonstrate the preparation of liposomal formulations that could be efficient to treat infection caused by any pathogen and/or any disease, but are in no way intended to limit the scope thereof.

Preparation of Immunoliposomes

Hybridomas producing monoclonal antibodies directed against human HLA-DR (clone 2.06, IgG$_1$), murine HLA-DR (clone Y-17, IgG$_{2b}$) and human CD4 (clone OKT4, IgG$_{2b}$) (American Type Culture Collection, Rockville, Md.) were isolated from ascites fluids of BALB/c mice and purified using a protein-G affinity column. Antibodies were sterilized on 0.22 μm low binding protein filters and stored at −20° C. in phosphate buffered saline (PBS, pH 7.4). Purity of antibodies was assessed by sodium dodecyl sulfate polyacrylamide gel electrophoresis (SDS-PAGE) under non-reducing conditions.

F(ab')$_2$ fragments of the 2.06 antibody were produced using an Immunopure IgG$_1$ Fab' and F(ab')$_2$ preparation kit (Pierce, Rockford, Ill.). In brief, the antibody was concentrated with a Centricon-100 (Amicon, Beverly, Mass.), resuspended in 0.5 ml of PBS and added to 0.5 ml of Immunopure IgG$_1$ mild elution buffer containing 1 mM cysteine. The solution was then incubated with an immobolized ficin column for 40 h at 37° C. The solution was then eluted with 4 ml of Immunopure binding buffer and fragments were separated on an Immunopure protein A column. The column retained Fc fragments and undigested IgG$_1$ whereas F(ab')$_2$ fragments were collected. Fractions containing F(ab')$_2$ were determined from absorbance readings at 280 nm and pooled together. The F(ab')$_2$ fragments (110 kD) were then concentrated using Centricon-50 and resuspended in phosphate-EDTA buffer (100 mM sodium phosphate and 5 mM EDTA, pH 6.0). F(ab')$_2$ fragments of Y-17 and OKT4 antibodies were produced following incubation of the antibodies with lysyl endopeptidase (in 50 mM Tris-HCl, pH 8.5) in an enzyme/substrate molar ratio of 1:50 for 3 h at 37° C. Lysyl endopeptidase cleaved IgG$_{2b}$ at Lys 228E/Cys 229 without perturbing disulfide bridges. The digestion products contained undigested IgG, F(ab')$_2$ and Fc fragments. The enzyme was removed by gel chromatography on a Sephadex G-25M column and fragments were fractionated with a protein A affinity chromatography column and resuspended in phosphate-EDTA.

F(ab')$_2$ fragments were incubated with 0.05 M of 2-mercaptoethylamine-HCl for 90 min at 37° C. under nitrogen atmosphere. This product cleaves the disulfide bridges between the heavy chains but preserves the disulfide linkages between the heavy and light chains. The solution was eluted on a Sephadex G-25M column pre-equilibrated with buffer and Fab' fragments were collected. Fractions containing Fab' were determined using a BCA protein assay reagent kit and pooled together. Fab' fragments were concentrated using Centricon-10, resuspended in buffer and kept under nitrogen atmosphere at 4° C. until coupling to liposomes. Purity of Fab' fragments was assessed by SDS-PAGE and their antigenic specificity was verified by flow cytometry using appropriate cells.

Liposomes of specific lipid compositions were prepared according to the method of thin lipid film hydration. In brief, the lipid mixture was dissolved in chloroform in a round-bottomed flask and the organic solvent was evaporated to form a thin lipid film. The lipid film was then hydrated with a buffer containing or not a drug to be encapsulated. In some experiments, a small proportion of radiolabelled lipids and drugs was added as radioactive tracers. Multilamellar vesicles were then sequentially extruded through polycarbonate membranes of defined pore sizes using a stainless steel extrusion device (Lipex Biomembranes, Vancouver, BC). Unencapsulated drug was removed by centrifugation of the liposomal preparation through a coarse Sephadex G-50 column and efficiency of drug entrapment was determined by radioactive countings. The mean vesicle size of the liposomes was evaluated with a submicron particle analyzer. For the coupling procedure, liposomes were incubated with freshly prepared Fab' fragments overnight at 4° C. under continuous agitation and under nitrogen atmosphere. Uncoupled Fab' fragments were removed through a Sepharose CL-4B size exclusion column (Sigma, St-Louis, Mo.) and the total amount of Fab' conjugated to liposomes was evaluated using a Coomassie protein assay reagent (Pierce, Rockford, Ill.).

Even though the following examples describe specific liposomal formulations, it is deemed that a family of liposomal formulations can be easily derived therefrom, without affecting the valuable properties thereof. Formulations of liposomes of the present invention include those having a mean particle diameter of any size. The formulations of liposomes of the present invention also include those prepared with any drug/lipid molar ratio. The following examples are intended to demonstrate specific liposomal formulations of drugs which could be very efficient for the treatment of infections caused by HIV, but are in no way intended to limit the scope thereof.

In Vitro Binding and Specificity of Immunoliposomes

The binding and specificity of conventional liposomes and anti-HLA-DR immunoliposomes were evaluated in different cell lines by flow cytometry assay. In brief, cells were maintained in complete culture medium of RPMI 1640 supplemented with 10% fetal bovine serum (FBS), 2 mM glutamine, 100 U/ml penicillin G and 100 µg/ml streptomycin at 37° C. under a 5% $CO_2$ atmosphere. Samples were washed with PBS and resuspended. The specificity of conventional liposomes and anti-HLA-DR immunoliposomes for the cells was determined by flow cytometry from the fluorescence associated to Dil (fluorochrome incorporated into the lipid membrane).

FIG. 1 shows the levels of binding of conventional liposomes and anti-HLA-DR ($IgG_1$, clone 2.06) immunoliposomes to three human lymphoma cell lines expressing different surface levels of the human HLA-DR determinant of MHC-II revealed by flow cytometry. As expected, anti-HLA-DR immunoliposomes did not bind to SUP-T1 cells that does not express HLA-DR on their surface (Panel A). In contrast, a very strong binding was observed following incubation of anti-HLA-DR immunoliposomes with both the HUT-78 and RAJI cells (Panels B and C) which bear important levels of human HLA-DR on their surface. These results clearly showed that liposomes bearing human anti-HLA-DR Fab' fragments were very specific to cells expressing HLA-DR determinant of MHC-II. The specificity of murine anti-HLA-DR immunoliposomes for I-E antigens present on mouse spleen cells has also been confirmed using a similar technical approach (data not shown).

Figure 2:
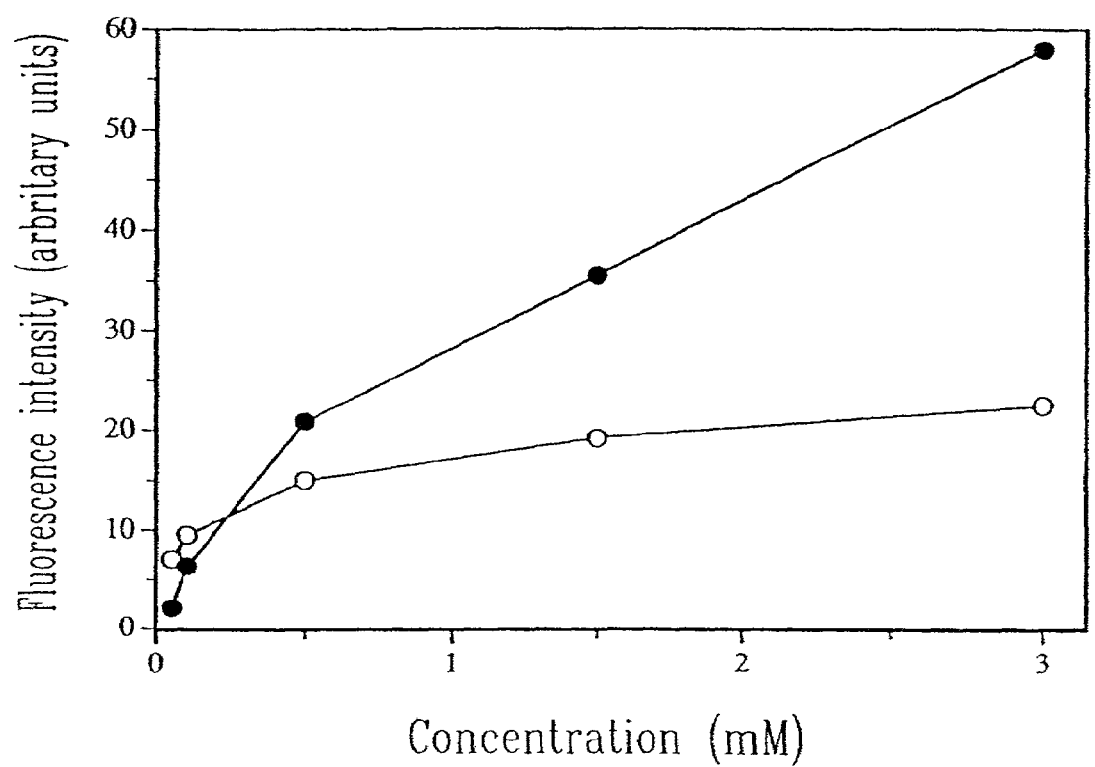
FIG. 2 shows the effect of liposomal concentration on the binding level of human anti-HLA-DR immunoliposomes with B lymphocytes as revealed by FITC conjugated goat anti-mouse IgG which binds to Fab' fragments (○) and by a fluorescent lipophilic DiI marker incorporated within the lipid membrane of anti-HLA-DR immunoliposomes (●).

The effect of liposomal concentration on the levels of binding of anti-HLA-DR immunoliposomes on B lymphocytes has also been investigated using two different fluorescent markers: i) a goat anti-mouse IgG (FITC) which binds to anti-HLA-DR Fab' fragments and ii) a fluorescent lipophilic Dil marker incorporated within the lipid membrane of immunoliposomes. Results showed that the binding level of anti-HLA-DR immunoliposomes with B cells, when incubated at 37° C., rapidly saturated when using FITC conjugated goat anti-mouse IgG as a marker whereas it increased linearly over the lipid concentration range when considering the fluorescence signal associated to Dil (FIG. 2). The saturation effect observed in the binding level of anti-HLA-DR immunoliposomes using FITC as a marker is attributed to the fact that a constant concentration of FITC-IgG was used for all liposomal concentration used. In contrast, as Dil is located in the lipid bilayer of immunoliposomes, the fluorescence intensity level was directly proportional to the lipid concentration used. Flow cytometry scans of HUT-78 cells incubated with Dil-labelled conventional liposomes as control clearly showed that there was no transfer of the fluorochrome from liposomes to cells (data not shown). Data were presented only for incubation of cells with anti-HLA-DR immunoliposomes at 37° C. as they are representative of in vivo conditions.

Tissue Distribution Studies

The accumulation of conventional and murine anti-HLA-DR immunoliposomes within lymphoid and non-lymphoid tissues has been investigated in mice. In brief, a single bolus injection of conventional liposomes, sterically stabilized liposomes, anti-HLA-DR immunoliposomes or sterically stabilized anti-HLA-DR immunoliposomes containing a small amount of radioactive lipid was administered subcutaneously in the upper back below the neck of female C3H mice (18-20 g; Charles River Breeding Laboratories, St-Constant, QC). At specific time, animals were sacrificed and blood was collected and separated by centrifugation. At the same time, selected tissues were collected, washed in PBS and weighed. Tissues and plasma were then treated with tissue solubilizer and decoloured in $H_2O_2$. Lipid levels in all samples were monitored by counting radioactivity. Six animals were used for each time point.

Figure 3:
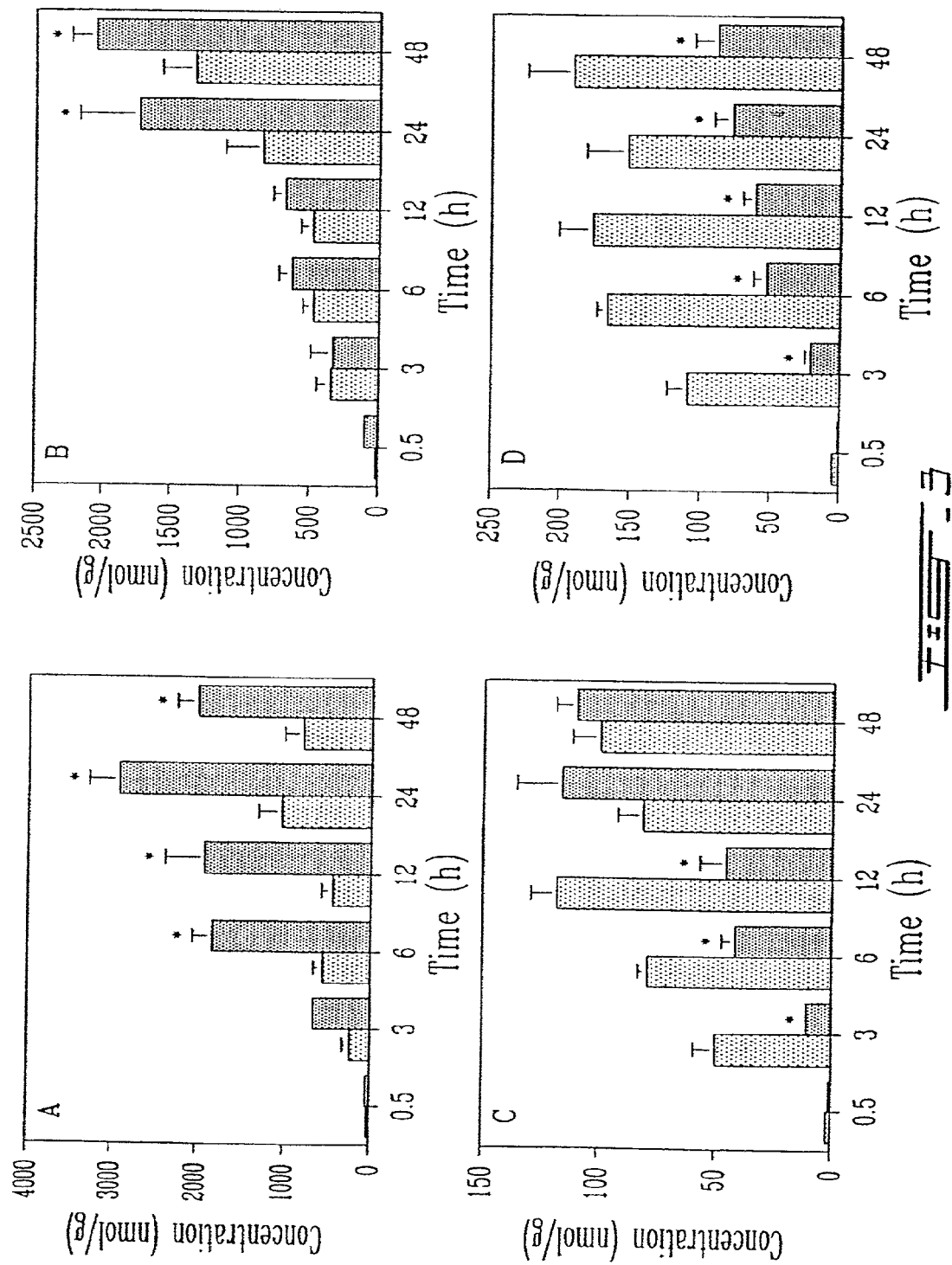
FIG. 3 shows the tissue distribution of conventional liposomes (dotted bar) and anti-HLA-DR immunoliposomes (solid bar) in A) brachial lymph nodes, B) cervical lymph nodes, C) liver and D) spleen following a single subcutaneous injection to mice. Values represent the mean (±SEM) obtained for six animals per group per time point. *Significantly different (p<0.01) when compared to conventional liposomes.

FIG. 3 shows the tissue distribution of conventional liposomes and anti-HLA-DR immunoliposomes in cervical lymph nodes, brachial lymph nodes, liver and spleen at different time intervals post-injection. Liposomes bearing murine anti-HLA-DR Fab' fragments targeted more efficiently the cervical lymph nodes when compared to that of conventional liposomes with a peak accumulation at 24 h post-injection. The accumulation of anti-HLA-DR immunoliposomes within brachial lymph nodes was very similar to that of conventional liposomes in the first 12 h post-injection but was significantly higher at 24 and 48 h post-injection. The concentration of anti-HLA-DR immunoliposomes within the liver was significantly lower than that of conventional liposomes for the first 12 h post-injection but reached similar values at 24 and 48 h post-administration whereas a lower accumulation of immunoliposomes was observed in the spleen for all time points studied.

Table 2 shows the area under the curve of anti-HLA-DR immunoliposomes and conventional liposomes in these different tissues. When compared to conventional liposomes, the subcutaneous administration of anti-HLA-DR immunoliposomes resulted in a 2.9 and 1.6 times greater accumulation in the cervical and brachial lymph nodes, respectively. On the other hand, the liposomal accumulation in the liver was similar for both liposomal preparations, whereas an approximately two-fold decreased accumulation was observed for anti-HLA-DR immunoliposomes in the spleen. In addition, results clearly showed that the subcutaneous administration route was very efficient for lymph node targeting as evidenced by the much higher accumulation of anti-HLA-DR immunoliposomes in these tissues when compared to that observed in the liver and spleen.

TABLE 2

Area under the curve of anti-HLA-DR immunoliposomes and conventional liposomes in different tissues following a single subcutaneous administration to C3H mice[a].

| Tissues | Immuno-liposomes | Conventional liposomes | Ratio immunoliposomes/ conventional liposomes |
|---|---|---|---|
| Cervical lymph nodes | 105.04 | 36.37 | 2.89 |
| Brachial lymph nodes | 61.65 | 39.20 | 1.57 |
| Liver | 4.03 | 4.21 | 0.96 |
| Spleen | 3.32 | 7.65 | 0.43 |

[a]Values expressed in μmoles lipids/g tissue/h, were calculated from the mean values of the tissue distribution profile using the trapezoidal rule.

The coupling of polyethyleneglycol (PEG) on the surface of liposomes is known to increase their ability to move through the lymph after subcutaneous injection and to decrease the rate of uptake into the MPS, increasing their residence time within plasma and/or lymph. Consequently, we have evaluated if attachment of anti-HLA-DR Fab' fragments to the end termini of PEG-coated liposomes could further improve their tissue accumulation compared to non-targeted sterically stabilized liposomes. Results showed that the concentration of both immunoliposomal formulations was higher in brachial and cervical lymph nodes than in other tissues suggesting that subcutaneous administration of immunoliposomes accumulates preferentially in regional lymph nodes (FIG. 4). In addition, sterically stabilized anti-HLA-DR immunoliposomes targeted more efficiently all tissues, with a peak of accumulation at 240 h in brachial, inguinal and popliteal lymph nodes and at 360 h or greater for cervical lymph nodes. Their was no significant differences in the accumulation of both immunoliposomal formulations at 6 h post-injection in lymph nodes and spleen, except for the popliteal lymph nodes, which are the farther lymph nodes from the injection site. The concentration of sterically stabilized anti-HLA-DR immunoliposomes in mesenteric lymph nodes reached a plateau at 24 h post-injection and the tissue distribution profile was similar to that observed in the spleen.

Table 3 shows the area under the curve of sterically stabilized anti-HLA-DR immunoliposomes and of anti-HLA-DR immunoliposomes in different tissues. Results clearly demonstrated that sterically stabilized anti-HLA-DR immunoliposomes accumulate much better than conventional anti-HLA-DR immunoliposomes in all tissues indicating that the presence of PEG has an important effect on the uptake of immunoliposomes by the lymphatic system.

TABLE 3

Area under the curve of sterically stabilized anti-HLA-DR immunoliposomes and conventional anti-HLA-DR immunoliposomes in different tissues, following the administration of a single subcutaneous dose to C3H mice.[a]

| Tissues | Sterically stabilized immuno-liposomes | Conventional immuno-liposomes | Ratio conv. immuno/ sterically stabilized immunoliposomes |
|---|---|---|---|
| Cervical lymph nodes | 1514.7 | 616.1 | 2.46 |
| Brachial lymph nodes | 1693.7 | 874.7 | 1.94 |
| Mesenteric lymph nodes | 16.0 | 5.5 | 2.91 |
| Inguinal lymph nodes | 34.8 | 15.8 | 2.20 |
| Popliteal lymph nodes | 70.8 | 26.3 | 2.69 |
| Liver | 61.5 | 25.5 | 2.41 |
| Spleen | 57.4 | 12.6 | 4.56 |

[a]Values, expressed in μmoles lipids/g tissues/h, were calculated from the mean values of the tissue distribution profile using the trapezoidal rule.

In another experiment, the concentration of the four types of liposomes (conventional liposomes, sterically stabilized liposomes, anti-HLA-DR immunoliposomes and sterically stabilized anti-HLA-DR immunoliposomes) was determined at 48 and 120 h after their subcutaneous administration to C3H mice. Results showed that the presence of PEG on the surface of conventional liposomes or anti-HLA-DR immunoliposomes had no effect on their lymphatic uptake in regional lymph nodes (brachial and cervical), but significantly increased their accumulation in other lymph nodes compared to conventional liposomes or anti-HLA-DR immunoliposomes (FIG. 5). On the other hand, there was no significant difference in the accumulation of sterically stabilized liposomes in the spleen when compared to conventional liposomes. In contrast, the concentration of sterically stabilized anti-HLA-DR immunoliposomes was much higher in the spleen when compared to anti-HLA-DR immunoliposomes. In addition, results showed that the presence of anti-HLA-DR Fab' fragments on both conventional and sterically stabilized liposomes greatly improved their accumulation in regional lymph nodes when compared to non-targeted liposomes.

We have next evaluated if the presence of anti-HLA-DR Fab' fragments at the end termini of PEG chains affect the tissue localization of liposomes. In this set of experiments, liposomal lipids (2.5 mg/ml) were first incubated with 10 μg/ml of Dil under darkness for 1 h at 60° C. with agitation. Unbound Dil was removed by centrifugation (300×g for 15 min at 4° C.) of the liposomal preparation through a coarse Sephadex G-50 column. A single bolus injection of sterically liposomes and sterically stabilized anti-HLA-DR immunoliposomes was administered subcutaneously in the upper back below the neck of female C3H mice. At specific times post-injection (24, 48 and 120 h), animals were sacrificed and selected tissues were removed. Tissues were then washed in PBS, embedded in OCT, frozen in liquid nitrogen and stored at −20° C. Tissue sections of 10 μm thickness were cut using a Jung Figocut 2800E from Leica Canada Inc. and deposited on slides pre-treated with 2% aminoalkysilane. Coated slides were immediately observed using a fluorescence microscope and pictures were taken. Dil fluorescence was observed with a rhodamine optics excitation filter.

Figure 6:
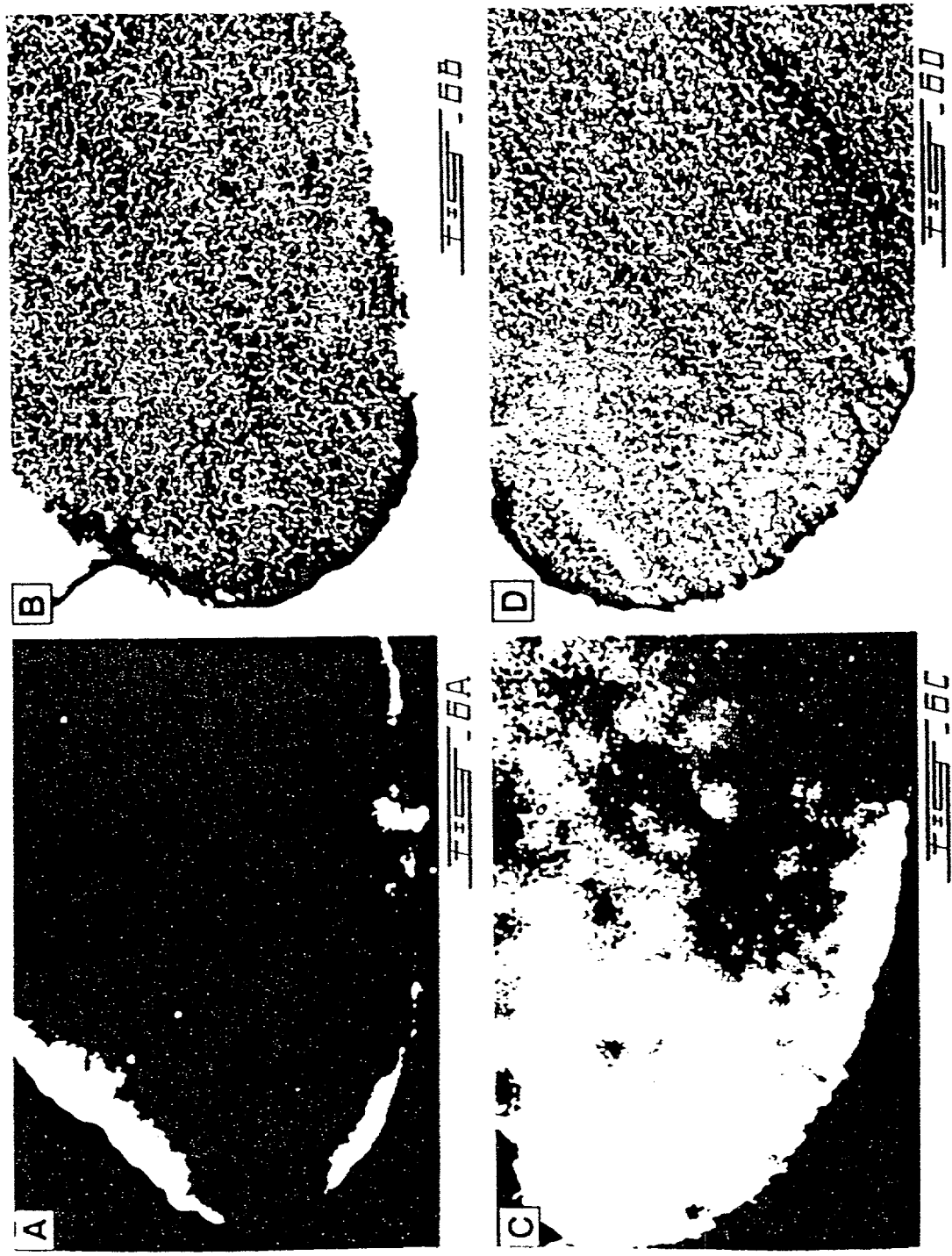
FIG. 6 shows fluorescent micrographs of brachial lymph nodes of C3H mouse at 120 h after the administration of a single subcutaneous dose of DiI-labelled sterically stabilized liposomes (Panel A) and sterically stabilized anti-HLA-DR immunoliposomes (Panel C) to mice. Panels B and D represent the corresponding hematoxylin eosin coloration of tissues. Figure shows the cortex area (C), the parafollicular area (PF), the medulla (M) and the lymphoid follicules (LF). Magnification: 250×.

FIG. 6 compares the localization of fluorescent sterically stabilized liposomes and sterically stabilized anti-HLA-DR immunoliposomes in brachial lymph nodes at 48 h after their subcutaneous administration in mice. Results showed that the localization of sterically stabilized anti-HLA-DR immunoliposomes was very different from that of sterically stabilized liposomes in brachial lymph nodes. Sterically stabilized liposomes were mainly localized in the subcapsular area, probably in the afferent lymphatic vessel and around the afferent area. In contrast, sterically stabilized anti-HLA-DR immunoliposomes mostly accumulated in the cortex in which follicles (B cells and FDCs) are located and in parafollicular areas in which T-cell, interdigitating dendritic cells and other accessory cells are abundant.

Figure 7:
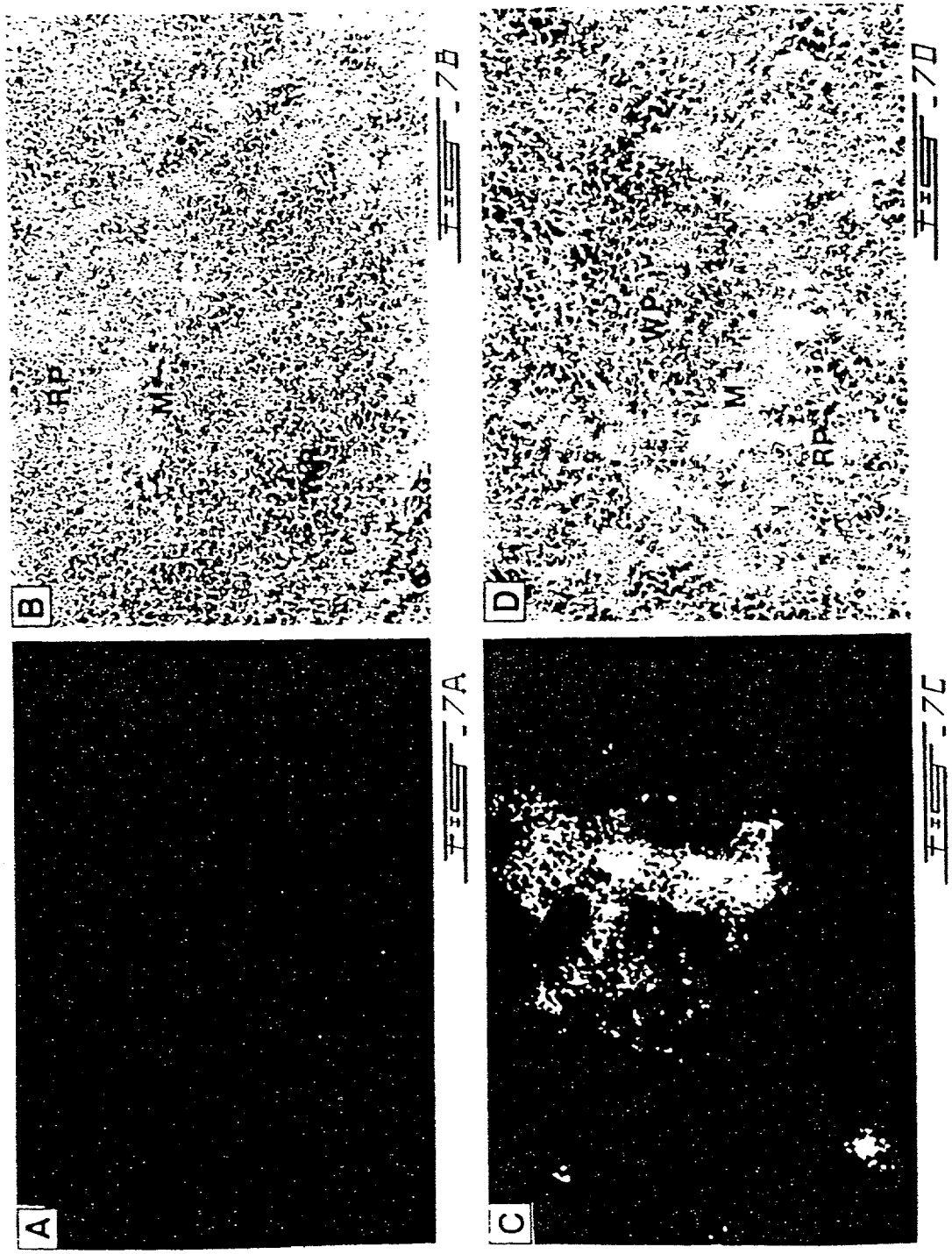
FIG. 7 shows fluorescent micrographs of spleen of C3H mouse at 48 h after the administration of a single subcutaneous dose of DiI-labelled sterically stabilized liposomes (Panel A) and sterically stabilized anti-HLA-DR immunoliposomes (Panel C) to mice. Panels B and D represent the corresponding hematoxylin eosin coloration of tissues. Figure shows the red pulp (RP) and the marginal zone (M) surrounding lymphoid follicule of the white pulp (WP). Magnification: 250×.

FIG. 7 compares the localization of sterically stabilized liposomes and sterically stabilized anti-HLA-DR immunoliposomes in spleen at 120 h after their subcutaneous administration to mice. Once again, results showed that the accumulation of sterically stabilized anti-HLA-DR immunoliposomes is better than sterically stabilized liposomes in this tissue but their localization was different. Sterically stabilized liposomes were localized mostly in the red pulp and the marginal zone of the white pulp whereas sterically stabilized anti-HLA-DR immunoliposomes were largely concentrated in the follicle of the white pulp and little in the marginal zone.

Figure 8:
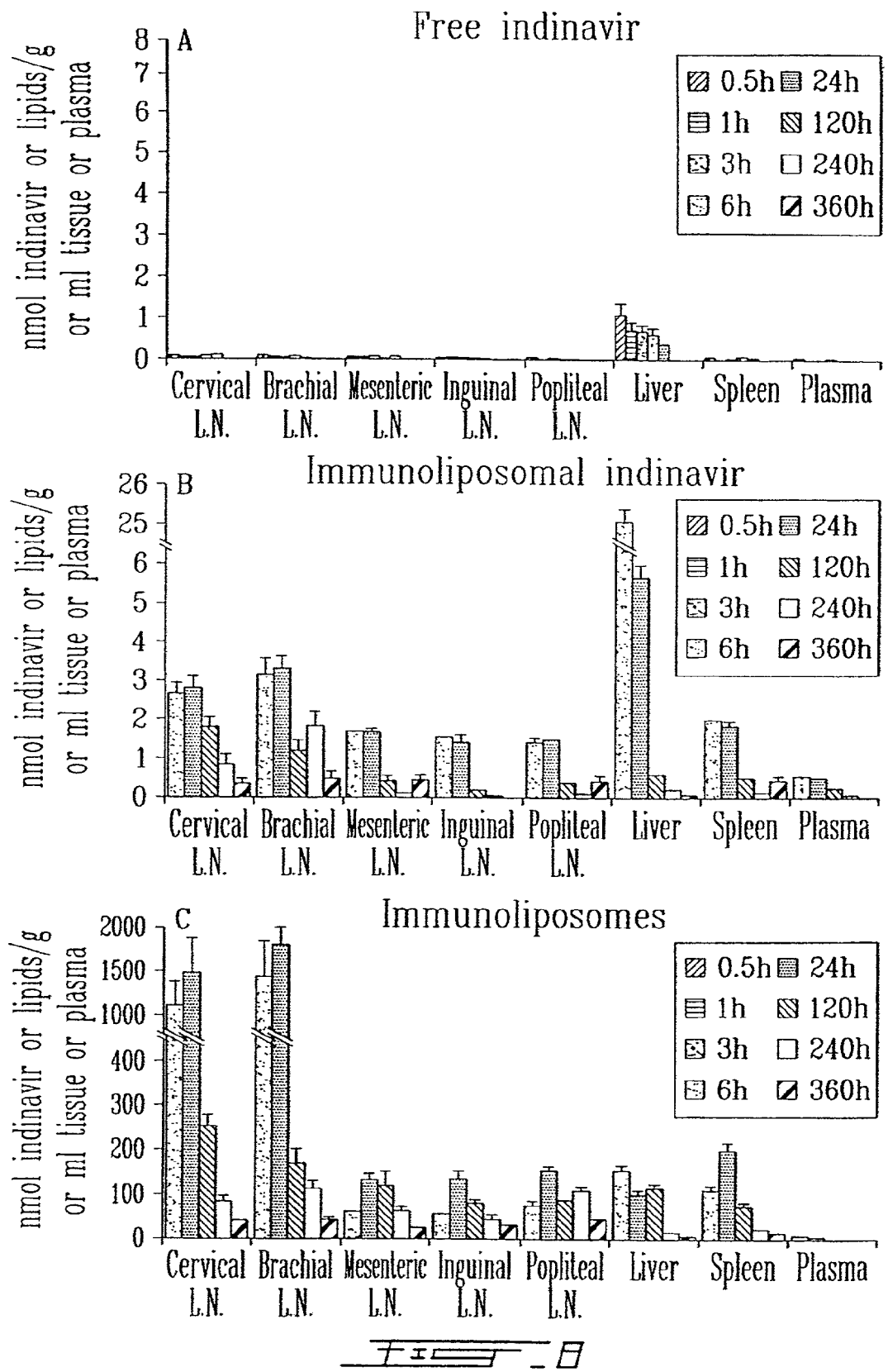
FIG. 8 shows the tissue and plasma distribution of free indinavir and of sterically stabilized anti-HLA-DR immunoliposomes containing indinavir as a function of time after a single bolus subcutaneous administration given in the upper back below the neck of C3H mice. Values represent the means (±SEM) obtained from 6 animals per group per time point.

The tissue distribution of free indinavir and sterically stabilized anti-HLA-DR immunoliposomes containing indinavir, has also been evaluated after a single subcutaneous administration to C3H mice (FIG. 8). Administration of free indinavir resulted in very low drug levels in all lymphoid tissues. Most of the injected drug accumulated in liver and was totally cleared within 24 h post-administration. In contrast, the incorporation of indinavir in sterically stabilized anti-HLA-DR immunoliposomes markedly improved the tissue and plasma distribution. Sterically stabilized anti-HLA-DR immunoliposomes were efficient in delivering high concentrations of the antiretroviral agent to all tissues and in plasma for up to at least 15 days post-injection. On the other hand, the tissue distribution profile of radiolabelled lipids was very similar to that of the immunoliposomal drug suggesting that indinavir was still associated to liposomes when taken up by tissues. Table 4 shows the corresponding area under the curve of free and immunoliposomal indinavir in tissues. Results clearly demonstrated that the incorporation of indinavir into anti-HLA-DR immunoliposomes greatly enhanced the drug accumulation in all tissues leading to a 21 to 126-fold increased accumulation when compared to the free agent. A greater drug concentration was observed in the cervical and brachial lymph nodes when compared to other tissues. Such site-specific drug targeting may allow less frequent administrations of drugs and at lower doses than conventional therapy reducing the marked toxicity actually seen in patients undergoing antiviral therapy with free agents.

In Vivo Toxicity Studies

The toxicity of indinavir, free and incorporated in sterically stabilized liposomes, has been evaluated after 10 consecutive subcutaneous injections to mice from histopathology studies and measurements of hepatic enzymes. In brief, female C3H mice (18-20 g) (group of 10 mice) were injected subcutaneously with 500 µl of indinavir, free or incorporated in sterically stabilized liposomes (34.3 mg indinavir/kg; 540 mg of lipids/kg body weight/day), once daily for 10 days and allowed to recover for 14 days. The choice of this dose was based on daily doses administered to HIV-infected patients. Animals treated with PBS and with a 0.86% DMSO solution were used as controls. Blood samples were collected on days 0, 11 and 24 biochemical analysis. Levels of aspartate aminotransferase (AST), alanine aminotransferase (ALT) and lactate dehydrogenase (LDH) were monitored in serum samples. On days 11 and 24, 5 mice/group were sacrificed and histopathological studies were performed on liver and spleen. In brief, tissues were fixed in a solution of 10% formalin for 4 days. After fixation, tissues were dehydrated and embedded in paraffin. Sections (5 µm thick) were placed on on gelatin-coated slides and allowed to dry for 4 h at 37° C. Slides were deparaffinized in toluene and hydrated in a series of graded ethanol solutions. During hydration, residual formalin was neutralized in ethanol-saturated picric acid. Slides were stained with hematoxylin-eosin and tissues were dehydrated, cleared and mounted with Permount (Fisher Scientific, Montréal, QC).

Figure 9:
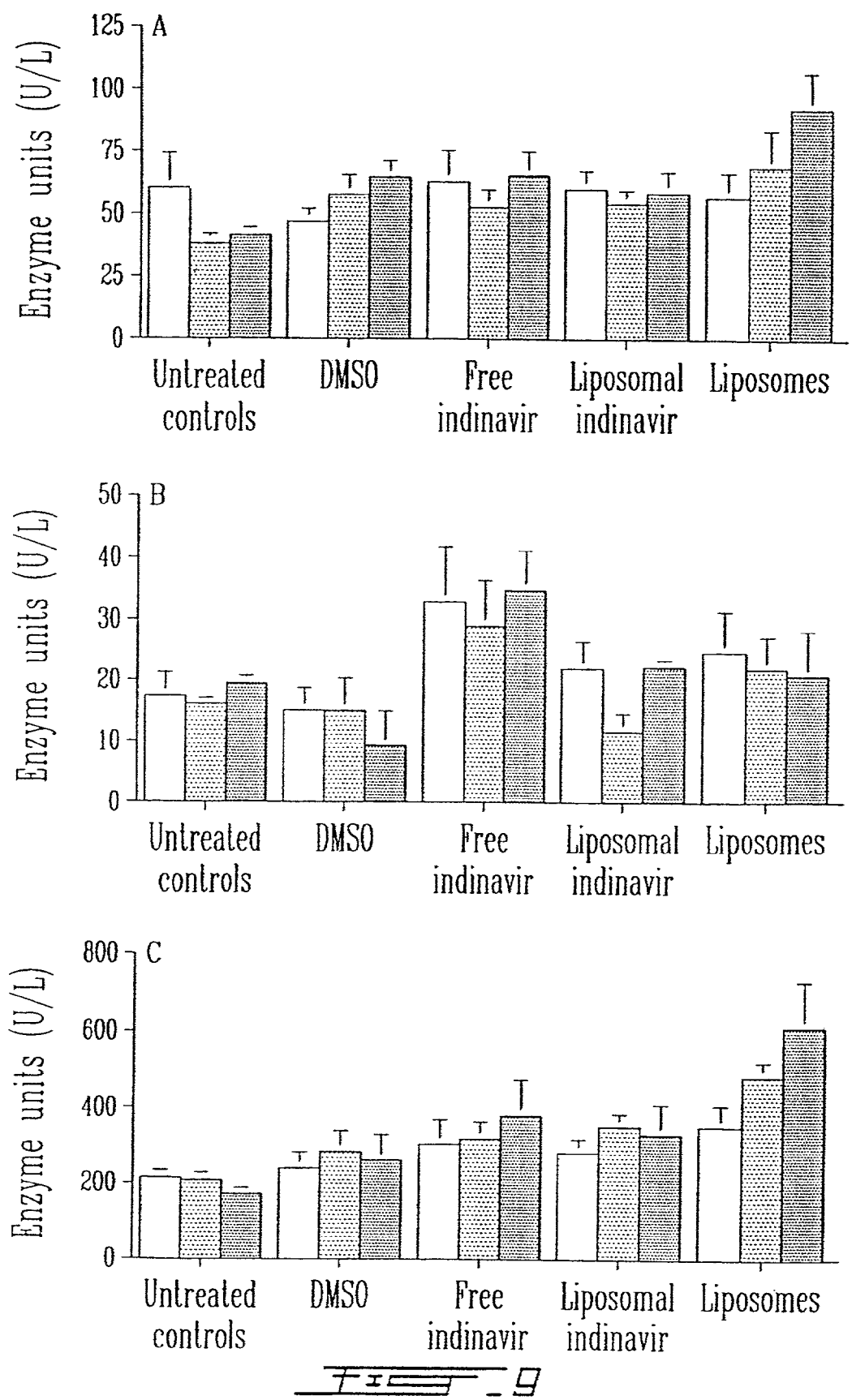
FIG. 9 shows the levels of aspartate aminotransferase (Panel A), alanine aminotransferase (Panel B) and lactate dehydrogenase (Panel C) in serum of mice after 10 daily subcutaneous administrations of 500 µl of free indinavir, indinavir incorporated in sterically stabilized liposomes and drug-free sterically stabilized liposomes (34.3 mg indinavir/kg; 540 mg of lipids/kg body weight/day). Levels of hepatic enzymes were monitored in serum samples taken on days 0 (open bars), 11 (dotted bars) and 24 (filled bars). Untreated animals and animals treated with a 0.86% DMSO solution were used as controls. Values represent the means (±SEM) obtained from 10 animals per group per time point.

No significant differences in the levels of hepatic enzymes were observed at the end of the treatment (day 11) and after the two weeks recovery (day 24) when compared to baseline and control untreated mice (FIG. 9). Only a moderate increase in the AST and LDH hepatic enzymes levels was observed in animals treated with drug-free liposomes. This mild toxicity could be attributed to lipid accumulation in liver but was not observed in liposomal formulations containing indinavir. Nevertheless, as anti-HLA-DR immunoliposomes are efficient to deliver indinavir to lymphoid tissues for up to 15 days post-administration, less frequent administrations than daily administrations for 10 days would be most likely required limiting thereby the potential hepatotoxicity of liposomes. Finally, histopathological studies revealed no significative damage to liver and spleen when compared to control group (data not shown).

TABLE 4

Area under the curve of free indinavir and sterically stabilized anti-HLA-DR immunoliposomes containing indinavir in tissues after a single subcutaneous administration C3H mice.[a]

| Tissues | Immunoliposomal indinavir | Free indinavir | Ratio immunoliposomal/ free indinavir |
| --- | --- | --- | --- |
| Cervical lymph nodes | 523.2 | 7.6 | 68.8 |
| Brachial lymph nodes | 617 | 4.9 | 126.0 |
| Mesenteric lymph nodes | 192.8 | 6.4 | 30.1 |
| Inguinal lymph nodes | 144.5 | 4.1 | 35.2 |
| Popliteal lymph nodes | 134.2 | 4.5 | 29.8 |
| Liver | 733.3 | 35.0 | 21.0 |
| Spleen | 211.3 | 5.3 | 39.9 |
| Plasma | 77.8 | 2.3 | 33.8 |

[a]Values, expressed in µmoles lipids/g tissues/h, were calculated from the mean values of the tissue distribution profile using the trapezoidal rule.

Immunogenicity Studies

The immunogenicity of conventional liposomes, sterically stabilized liposomes bearing anti-HLA-DR Fab' fragments or complete IgG antibody ($2 \times 10^{-10}$ mol of protein/ µmol lipid) or a mixture of sterically stabilized liposomes liposomes and antibodies has been investigated in rats after four repeated subcutaneous administrations given on days 0, 7, 14 and 21. in brief, blood samples were collected at different time points (day 0, 6, 13, 20 and 27) an antibody titers in serum samples were quantified by sandwich ELISA using Nunc MaxiSorp microtiters plates. In brief, plates were coated with 5 µg/ml (100 µl/well) of the tested proteins (Fab' fragments, whole IgG or irrelevant protein, BSA) for 2 h at 37° C. Afterwards, plates were washed three times with PBS containing 0.2% Tween-20 and incubated with blocking buffer for 30 min at 37° C. Plates were washed again and serum dilutions from immunized animals were added (100 µl/well), incubated for 1 h at 37° C. and washed again to remove unbound proteins. A biotin-conjugated goat anti-rat IgG solution (100 µl/well, diluted 1:50000 in blocking buffer) was added to each well and plates were incubated for 1 h at room temperature. Unbound antibodies were washed with PBS containing 0.2% Tween-20 and horseradish peroxydase conjugated streptavidin (100 µl/well, diluted 1:4000 in PBS containing 2% BSA and 0.05% Tween-20) was added and incubated for another 30 min at room temperature. After three washes, hydrogen peroxide 3,3',5, 5' tetramethylbenzidine (100 µl/well) was added to the solution and after a 30 min incubation at room temperature, the reaction was stopped by adding 50 µl of a 1 M $H_3PO_4$ solution. Absorbance was read at 450 nm on a microplate reader.

Figure 10:
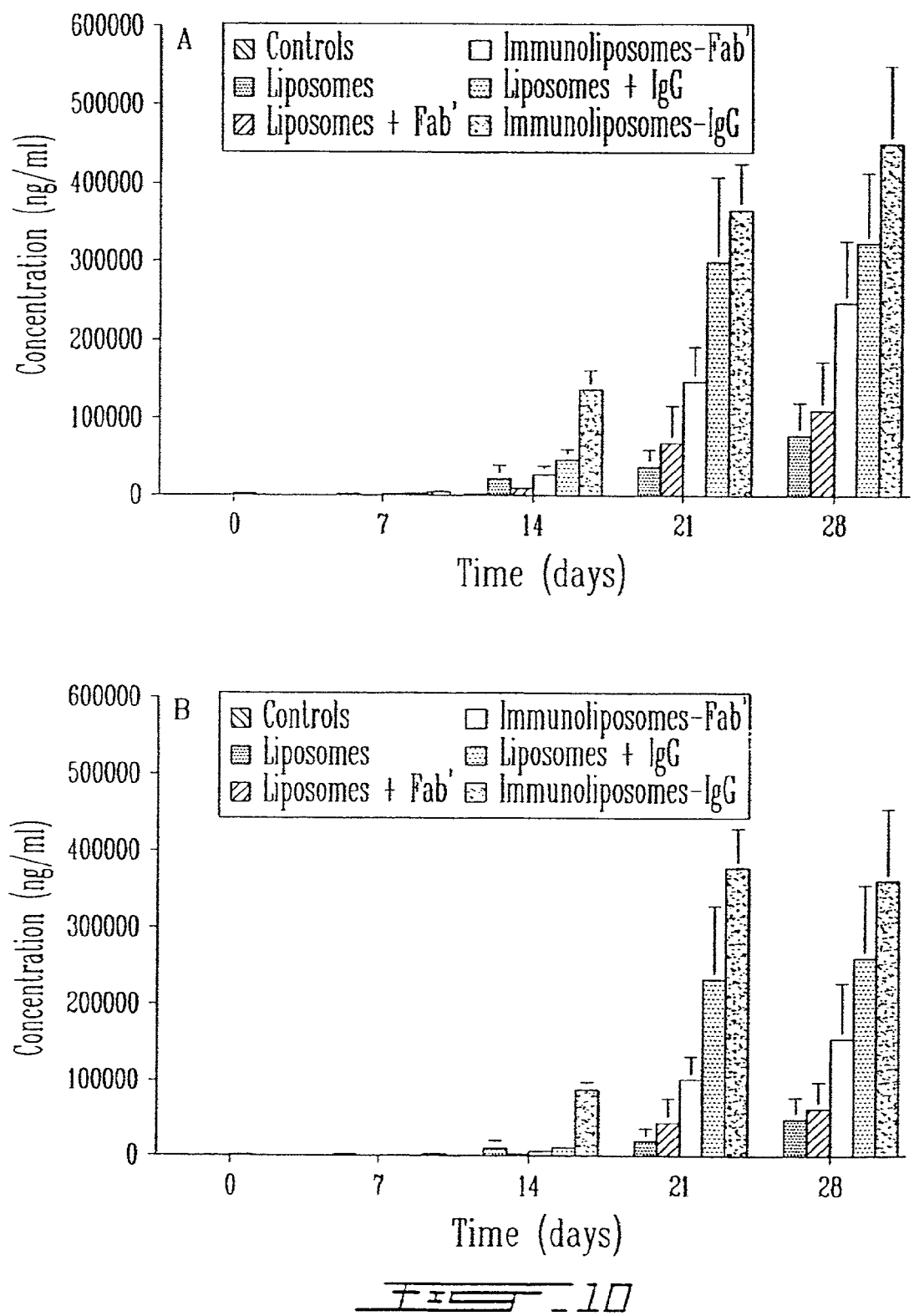
FIG. 10 shows the levels of antibodies in serum samples of rats after four repeated subcutaneous injections of sterically stabilized liposomes, sterically stabilized anti-HLA-DR immunoliposomes or a mixture of sterically stabilized liposomes and antibodies on A) Y-17 IgG-coated plates and B) Y-17 Fab' fragments-coated plates. Values represent the means (±SEM) obtained from 5 animals per group per time point.

FIG. 10 shows the levels of antibodies in serum samples of rats after four repeated subcutaneous injections of sterically stabilized liposomes, sterically stabilized anti-HLA-DR immunoliposomes or a mixture of sterically stabilized liposomes and antibodies. As expected, liposomes bearing Fab' fragments were 2.3-fold less immunogenic than liposomes bearing the entire IgG. Lower levels of rat antibodies were detected on Fab' fragments-coated plates, suggesting that the immune response is principally directed against the Fc portion of immunoglobulin. However, the concentration of antibodies in serum increased rapidly with the number of injections suggesting that the primary response is first directed against the Fc portion, but as the immune response mature, other antibodies are developed against the Fab' portion of the antibody. In order to verify the specificity of these antibodies, ELISA was performed with irrelevant protein BSA and no signal was detected (data not shown). Liposomes bearing Fv fragments, which constitute the smallest part of the immunoglobulin that keeps affinity for ligand, could possibly reduce induction of immune response associated with repeated administrations of immunoliposomes.

In Vitro Efficacy Studies

The ability of indinavir, free or encapsulated in sterically stabilized liposomes or sterically stabilized anti-CD4 immunoliposomes, to inhibit HIV-1 replication has been evaluated in SUPT-1 cells from measurements of reverse transcriptase activity. Briefly, $1.25 \times 10^5$ cells were incubated with HIV-1 (strain NL4-3; 25 ng of p24) and different concentrations of free indinavir or liposomal formulations of indinavir (10 to 100 nM) in a final volume of 500 µl. Cells were maintained in RPMI 1640 supplemented with 10% FBS, 2 mM L-glutamine, 100 U/ml penicillin G and 100 mg/ml streptomycin. Twice a week, 50 µl of supernatant were collected and stored at −20° C. until measurements of reverse transcriptase activity and 200 µl of cell suspension was removed for cell viability assay. Thereafter, 250 µl of fresh culture medium were added in each well. Reverse transcriptase activity was measured by incubating supernatant with 10 µl of a solution A (5 mM dithiothreitol, 50 mM KCl, 0.05% Triton X-100) and 40 µl of a solution B (5 mM $MgCl_2$, 0.5 M EGTA, 0.04 mg of poly(rA)-oligo(dT)$_{12-18}$, 3 mCi $^3$H-TTP (40 to 70 Ci/mmol)). After an 1 h incubation period at 37° C., samples were precipitated onto glass fiber filters by using a cell harvester system and reverse transcriprase activity was measured using a liquid scintillation counter (1205 Beta-plate; Wallac Oy, Turku, Finland).

Figure 11:
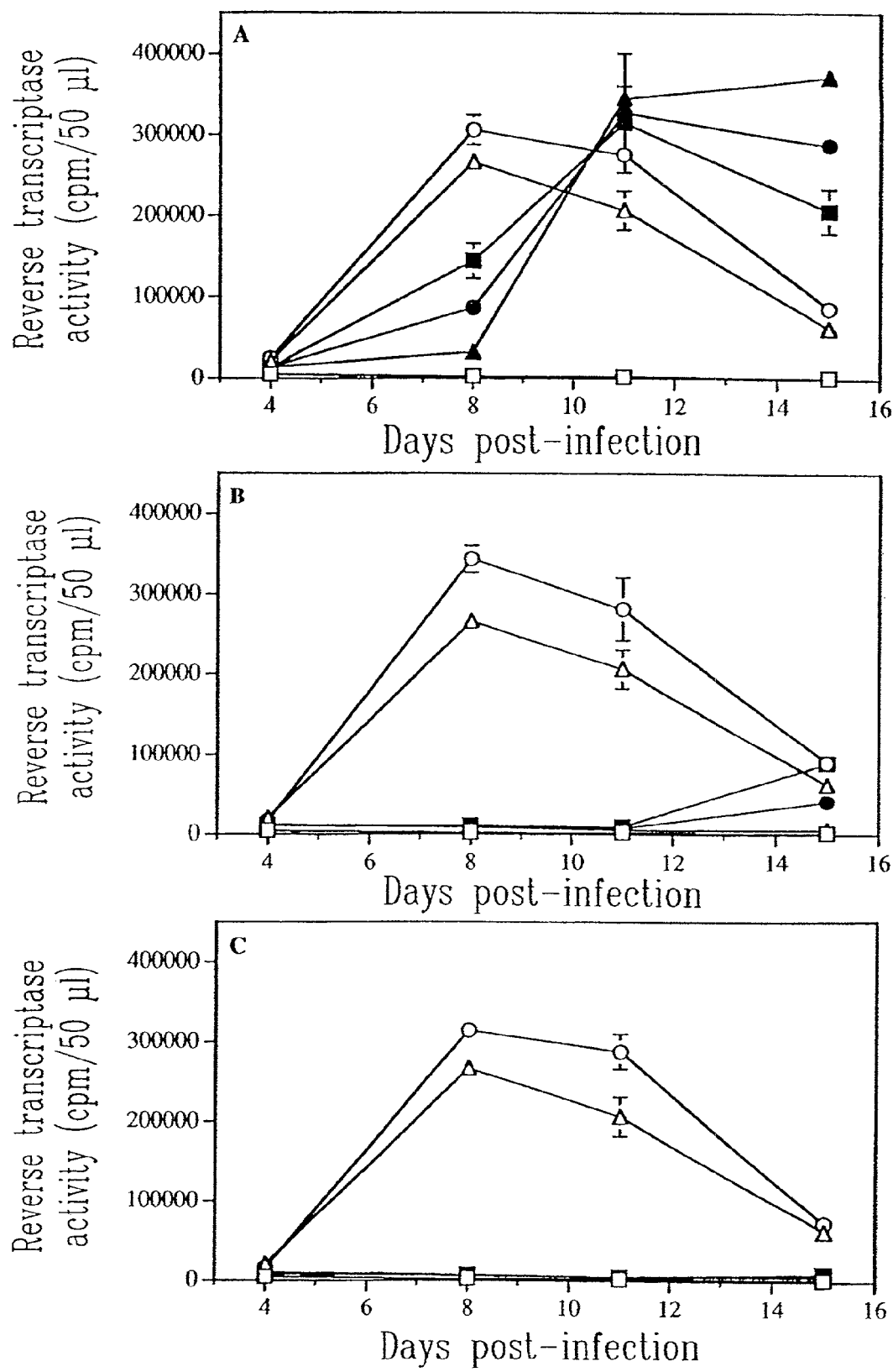
FIG. 11 shows the in vitro efficacy of free indinavir (▲), sterically stabilized liposomes containing indinavir (●) and sterically stabilized anti-CD4 immunoliposomes containing indinavir (■) to inhibit HIV-1 replication in SUPT-1. Antiviral efficacy was evaluated using a concentration of indinavir of 10 nM (panel A), 50 nM (panel B) and 100 nM (panel C). Uninfected cells (□), untreated infected cells (Δ) and infected cells treated with a solution of DMSO at the same concentration than those used for the preparation of the indinavir solutions (○) were used as controls. Results represent the average of triplicate incubations from one experiment typical of 3.

FIG. 11 shows the efficacy of indinavir, free or incorporated in sterically stabilized liposomes or sterically stabilized anti-CD4 immunoliposomes, to inhibit HIV-1 replication in CD4+ T lymphocytes. Globally, both liposomal and immunoliposomal formulations of indinavir were as efficient than the free agent to inhibit HIV-1 replication in this cell line. The reduced efficacy of all preparations at low concentrations of indinavir as a function of time post-infection is normal since, in our experimental set-up, a certain amount of the indinavir formulations was removed periodically from culture medium reducing thereby, their efficacy against HIV-1 replication. However, because our immunoliposomes allow efficient drug targeting of HIV reservoirs, the potential therapeutic advantages of immunoliposomes over the free agent for the treatment of HIV infection are expected to be observed under in vivo situations.

The efficacy of different formulations of amphotericin B (AmB) to inhibit cell-free T- or macrophage-tropic HIV-1 strains that have incorporated or not host-derived HLA-DR proteins has been evaluated in HLA-DR/negative (NEG) 1G5 T-cells and HLA-DR/positive (POS) Mono Mac 1 cells. In brief, 1G5 cells were infected with HIV-1$_{NL4-3}$ (10 ng of p24) while Jurkat E6.1 cells were infected with luciferase-encoding pseudotyped virions (10 ng of p24) for 2 h at 37° C. in a final volume of 200 µl of complete culture medium. Afterwards, cells were washed with PBS, resuspended in 200 µl of medium and transferred to a 96-well flat-bottomed tissue culture plate and allowed to grow for 72 h at 37° C. in a 5% $CO_2$ atmosphere. In some experiments, HIV-1$_{NL4-3}$ or 1G5 cells were pretreated with AmB (0-10 µg/ml) for 60 min at 37° C. in a final volume of 100 µl of complete culture medium prior to infection. In another set of experiments, AmB was added 2 h after the adsorption period and maintained in contact with cells for 72 h. Infection was monitored by measuring the luciferase activity. In brief, 100 µl of cell-free supernatant was withdrawn from each well and 25 µl of a cell culture lysis buffer were added before incubation at room temperature for 30 min. Thereafter, an aliquot of this cell lysate (20 µl) was mixed with 100 µl of luciferase assay buffer and activity was evaluated using a microplate luminometer.

HLA-DR/POS HIV-1$_{NL4-3}$, HLA-DR/NEG HIV-1$_{NL4-3}$ or HIV-1$_{ADA}$ (10 ng of p24) were treated with different concentrations of free or anti-HLA-DR immunoliposomes containing AmB (0-5 µg/ml) or with the corresponding amount of conventional liposomes or anti-HLA-DR immunoliposomes for 1 h at 37° C., in a final volume of 100 µl of complete culture medium. Afterwards, 1G5 cells were infected with equal amounts of pretreated HLA-DR1/POS HIV-1$_{NL4-3}$, HLA-DR/NEG HIV-1$_{NL4-3}$ (10 ng of p24) for 2 h at 37° C., in a final volume of 200 µl of complete culture medium. Mono Mac 1 cells were infected with HIV-1$_{ADA}$ (10 ng of p24) as described above. Cells were then washed with PBS, resuspended in 200 µl of complete culture medium, and transferred to a 96-well flat-bottomed tissue culture plate. After a 72 h incubation period at 37° C. in a 5% $CO_2$ atmosphere, luciferase activity was monitored as described above.

Figure 12:
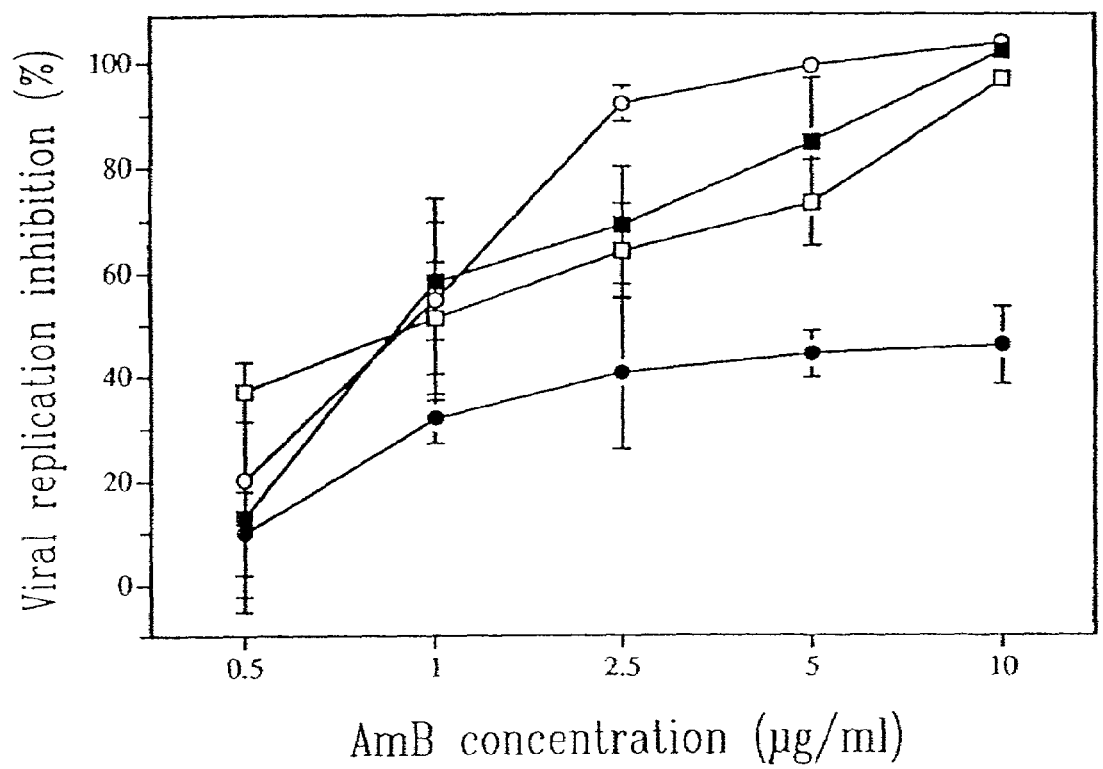
FIG. 12 shows the effect of AmB on HIV-1$_{NL4-3}$ viral replication inhibition in 1G5 cells under various experimental conditions. In a first set of experiments, cell-free virus (open circle) or 1G5 cells (solid square) were pretreated with increasing concentrations of AmB for 1 h at 37° C., washed and maintained in fresh culture medium in the absence of AmB. In a second set of experiments, AmB and the virus were added simultaneously to cells and incubation was made during the first two hours of infection (open square). In a third set of experiments, AmB was added to HIV-1$_{NL4-3}$ infected cells after a 2 h adsorption period and maintained in contact with cells for 72 h (solid circle). Luciferase activity was measured at 72 h post-infection. Values represent the average (±SD) of triplicate incubations from one experiment typical of 3.

FIG. 12 shows the effect of AmB concentration on HIV-1$_{NL4-3}$ viral replication inhibition under various experimental conditions. Pretreatment of cell-free viral particles with AmB for 1 h at 37° C. inhibited HIV-1 replication in a dose-dependent manner. About 50% of viral particles were inactivated after pretreatment with 1 µg AmB/ml, whereas a complete abrogation of viral replication was obtained at 5 µg AmB/ml. When 1G5 cells were pretreated with AmB, a complete inhibition of HIV-1$_{NL4-3}$ replication was observed at a concentration of 10 µg AmB/ml. Similarly, when the virus and AmB were added simultaneously to cells (i.e. no pretreatment), complete inhibition of HIV-1 replication occurred at 10 μg AmB/ml. Finally, when AmB was added to HIV-1$_{NL4-3}$ infected cells, viral replication was inhibited only to 40% with 10 μg AmB/ml. Incubation of 1G5 cells for 72 h with AmB in the range of concentration tested did not affect the cellular viability (data not shown). Altogether, these results suggest that AmB may exert a direct effect on cell-free virions and that AmB has to be present in the first period of viral infection to achieve a complete inhibitory effect on viral replication. To test whether AmB blocks infection at the virus entry level, we used HIV-1-based luciferase reporter viruses with HXB2, AML-V or VSV-G env. The luciferase reporter viruses infect cells in a single round but are not competent for further replication. Therefore, measurement of luciferase activity with such pseudotypes viruses allows to evaluate the efficacy of AmB to inhibit the entry of viruses having different envelopes. AmB at a concentration of 5 μg/ml was efficient to inhibit infection of a T-cell line with all three pseudotyped virions suggesting that AmB inhibition of HIV-1 infection is not specific to HIV-1 envelope proteins (data not shown).

Figure 13:
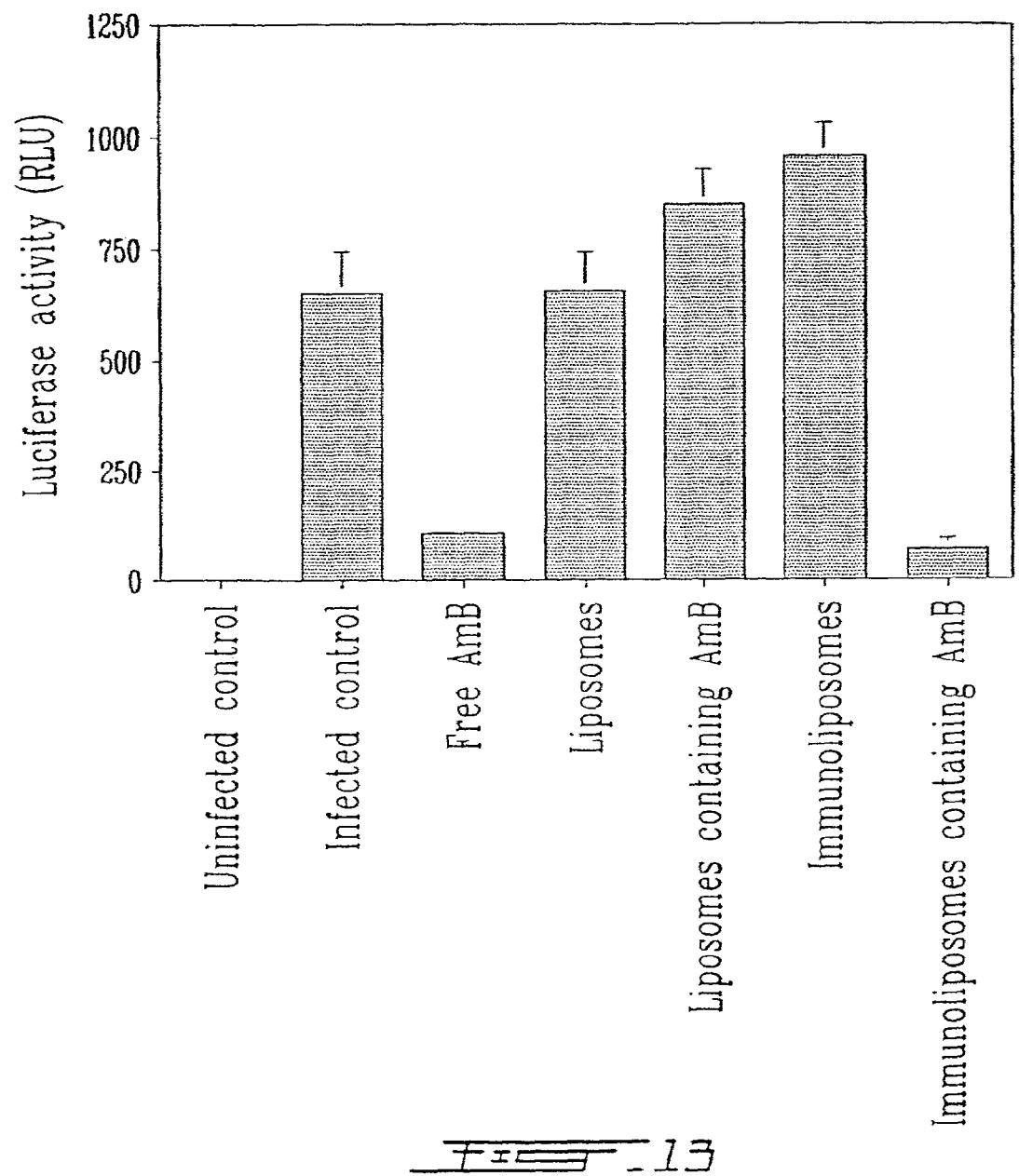
FIG. 13 shows the effect of free AmB, conventional liposomes, conventional liposomes containing AmB, anti-HLA-DR immunoliposomes, and anti-HLA-DR immunoliposomes containing AmB on HLA-DR/POS HIV-1$_{NL4-3}$ replication. HLA-DR/POS HIV-1$_{NL4-3}$ were treated with 5 μg AmB/ml or the corresponding amount of liposomes for 1 h at 37° C. 1G5 cells were then infected (10 ng/10$^5$ cells) for 2 h at 37° C., washed and allowed to grow in fresh culture medium in the absence of AmB or liposomes. Uninfected cells and untreated infected cells were used as controls. Luciferase activity was measured at 72 h after infection. Values represent the average (±SD) of triplicate incubations from one experiment typical of 3.

Since pretreatment of HIV-1$_{NL4-3}$ with AmB at a concentration of 5 μg/ml completely inhibited viral replication in 1G5 cells, we have next evaluated the capacity of anti-HLA-DR immunoliposomes containing this concentration of AmB to target and inhibit cell free virus. As expected, treatment of HIV-1 particles expressing host-encoded HLA-DR with anti-HLA-DR immunoliposomes containing AmB inhibited HIV-1 replication in 1G5 T-cells (FIG. 13). In contrast, AmB incorporated in conventional liposomes did not affect HIV infectivity at this concentration suggesting that inhibition of HIV particles is due to specific targeting of HLA-DR host-embedded molecules. On the other hand, both conventional liposomes and anti-HLA-DR immunoliposomes without AmB did not inhibit viral replication. All formulations tested were not toxic to 1G5 cells (data not shown).

Figure 14:
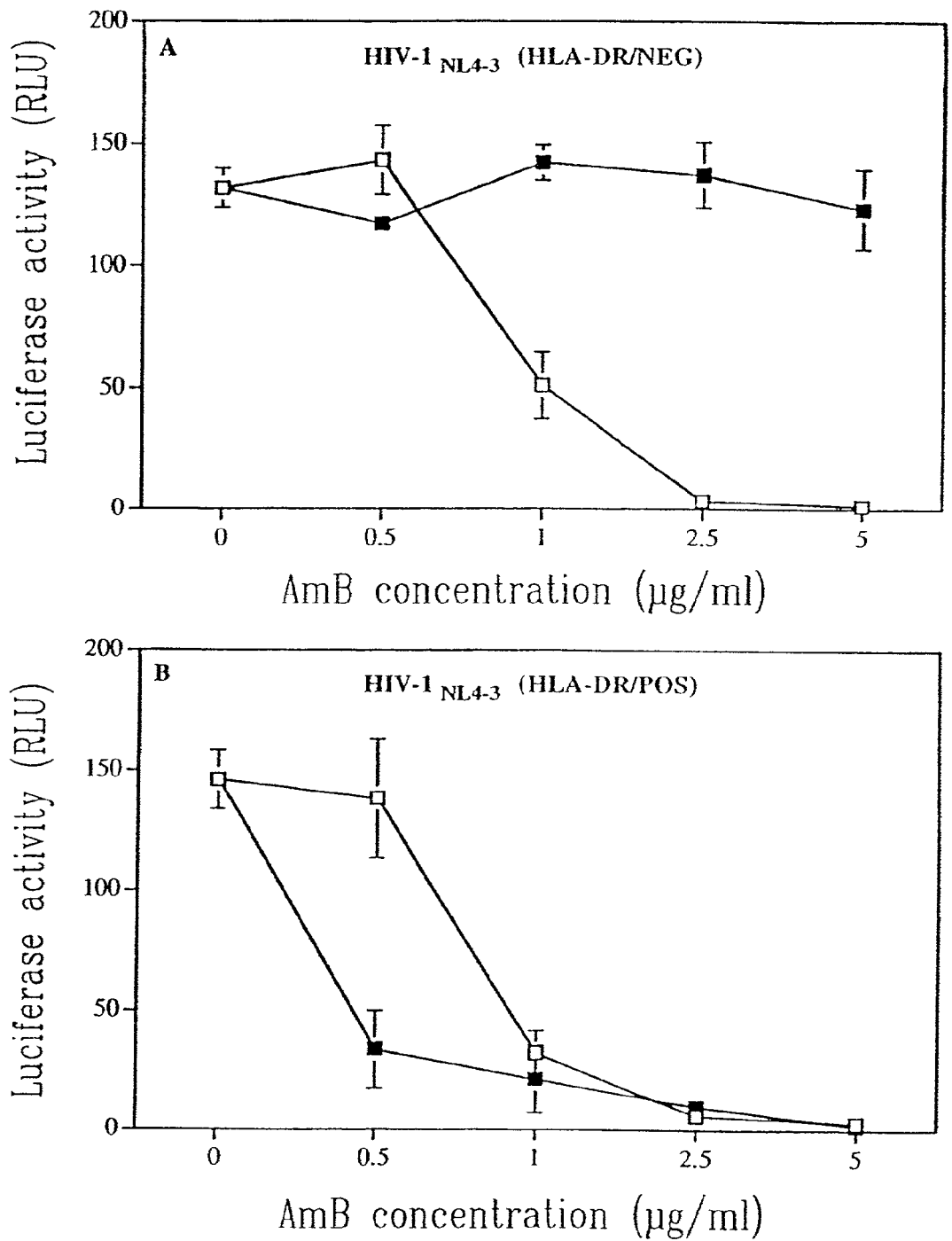
FIG. 14 shows the effect of free AmB (empty square) and anti-HLA-DR immunoliposomes containing AmB (solid square) on A) HLA-DR/NEG HIV-1$_{NL4-3}$ and B) HLA-DR/POS HIV-1$_{NL4-3}$ replication in HLA-DR/NEG 1G5 cells following pretreatment of virus with different concentrations of AmB for 1 h at 37° C. 1G5 cells were infected with pretreated virus (10 ng/10$^5$ cells) for 2 h at 37° C., washed and allowed to grow in fresh culture medium in the absence of AmB or anti-HLA-DR immunoliposomes. Luciferase activity was measured at 72 h post-infection. Values represent the average (±SD) of triplicate incubations from one experiment typical of 3.

To investigate whether anti-HLA-DR immunoliposomes containing AmB inhibit specifically the infectivity of HIV-1 particles that have incorporated HLA-DR molecules, HLA-DR/NEG HIV-1$_{NL4-3}$ and HLA-DR/POS HIV-1$_{NL4-3}$ were incubated with different concentrations of free AmB and anti-HLA-DR immunoliposomes containing AmB. In contrast to HLA-DR/POS HIV-1$_{NL4-3}$, AmB incorporated in anti-HLA-DR immunoliposomes had no effect on HLA-DR/NEG HIV-1$_{NL4-3}$ replication at concentration between 0-5 μg AmB/ml (FIG. 14). Approximately 77% of HLA-DR/POS HIV-1$_{NL4-3}$ replication was inhibited with anti-HLA-DR immunoliposomes containing AmB (0.5 μg/ml) whereas free AmB had no significant antiviral activity at this concentration. These results confirm that anti-HLA-DR immunoliposomes containing AmB specifically targets and inhibits HLA-DR expressing HIV-1, and that, more efficiently than free AmB.

Figure 15:
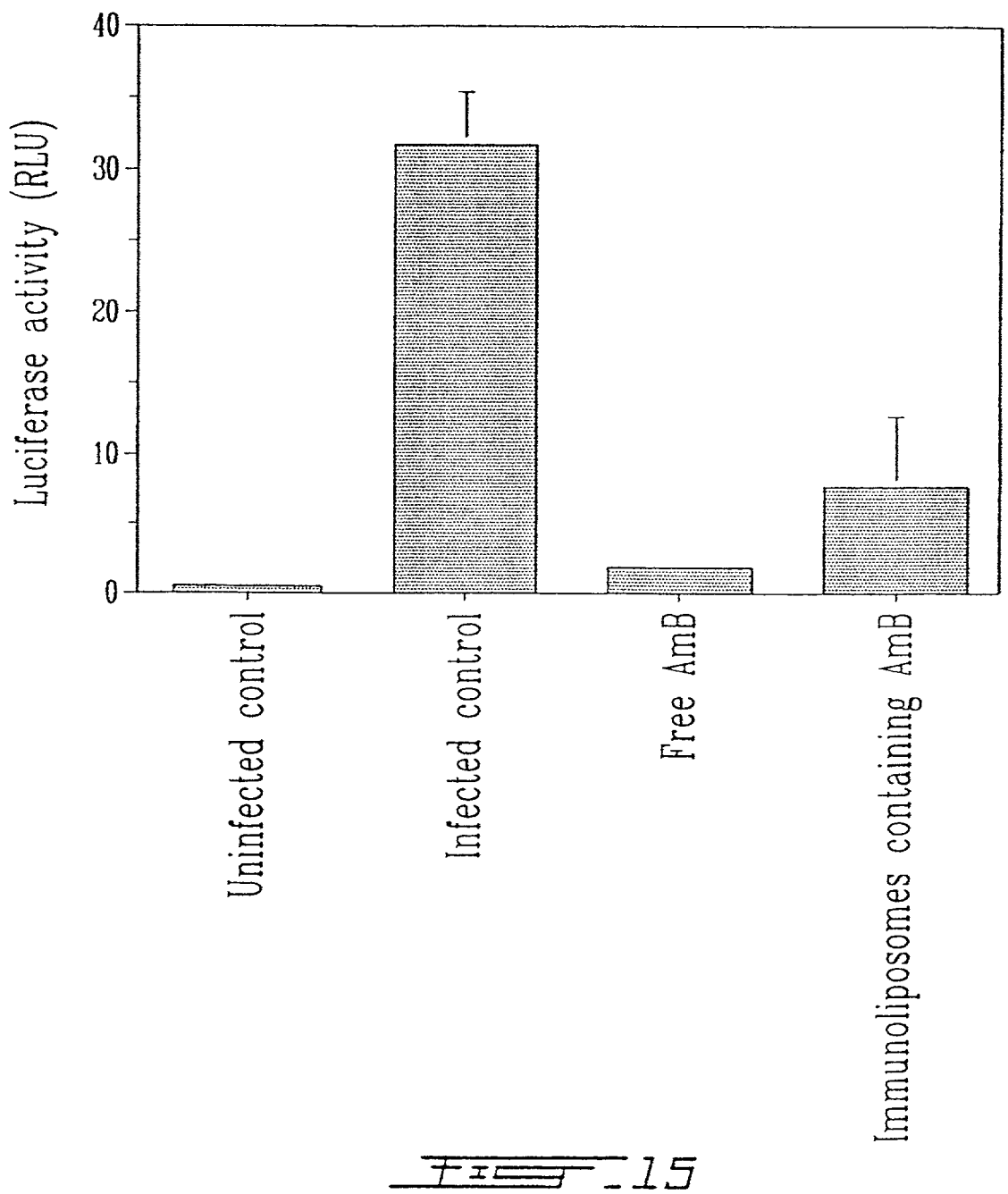
FIG. 15 shows the effect of free AmB and anti-HLA-DR immunoliposomes containing AmB on HLA-DR/NEG HIV-1$_{ADA}$ replication in the monocyte/macrophage HLA-DR/POS Mono Mac 1 cell line following pretreatment of virus with AmB (5 μg/ml) for 1 h at 37° C. Mono Mac 1 cells were infected with pretreated virus (10 ng/10$^5$ cells) for 2 h at 37° C., washed and allowed to grow in fresh culture medium in the absence of AmB or immunoliposomes. Uninfected cells and untreated infected cells were used as controls. Luciferase activity was measured at 72 h post-infection. Values represent the average (±SD) of triplicate incubations from one experiment typical of 3.

We have next evaluated the efficacy of AmB incorporated in anti-HLA-DR immunoliposomes to inhibit viral replication of the macrophage-tropic HIV-1$_{ADA}$ in the monocyte/macrophage HLA-DR/POS Mono Mac 1 cell line. This cell line represents an appropriate model system to study HIV-1 infection as an immortalized cell line which parallels primary MDM properties such as necessary surface receptor/co-receptors mediating HIV-1 infection by M-tropic strains of HIV-1 and infection kinetics. Surprisingly, anti-HLA-DR immunoliposomes containing AmB were as efficient as free AmB to inhibit HLA-DR/NEG HIV-1$_{ADA}$ replication in a HLA-DR/POS cell line (FIG. 15) without significant toxicity for both formulations (data not shown). These results suggest that anti-HLA-DR immunoliposomes containing AmB could protect HLA-DR/POS cells against virus infection.

With a chronic disease such as HIV infection we need innovatives approaches that could improve the treatment of HIV-infected individuals. Therefore, more potent antiretroviral drugs or the use of alternative approaches that block the potential spread of virus within lymphoid tissues, their main reservoir, are urgently needed. The use of immunoliposomal drugs represents an innovative approach to inhibit virally-infected cells and cell-free particles diminishing, thereby, the viral load within lymphoid organs. Such site-specific drug targeting may allow less frequent administrations of antiviral agents and at lower doses than conventional therapy reducing therefore the marked toxicity actually seen in patients undergoing antiviral therapy with free drugs. In addition, the subcutaneous administration of liposomal drugs may lead to the generation of new modes of delivery in the future such as subcutaneous pumps. The incorporation of anti-HIV agents in anti-HLA-DR and anti-CD4 immunoliposomes could represent a novel therapeutic strategy to specifically target HIV-1 cellular reservoirs and cell-free virus with the ultimate goal of treating more efficiently patients afflicted with HIV/AIDS.

Methods of Formulation and Methods of Use

From the above detailed compositions or formulations, the skilled artisan will readily appreciate that a method of formulating the compositions is obviously contemplated and inherent to this invention. This method comprises the step of coupling the ligand to the lipid-comprising vesicle as disclosed and covered by the methodology used and practiced the specific examples. Further, the use of this formulation for treating a patient affected by an infectious disease, which comprises the step of administering the above compositions or formulations is also within the scope of the invention. The treatment may be either a passive immunization against the infectious agent or destablization of the membranes of the host cell or the infectious agent, or delivering the drug to the host cell or the infectious agent. Finally, this invention has been described hereinabove and it may be subject to variations without departing from the spirit and teachings of this invention. These variations are within the scope of this invention, as defined in the appended claims.

What is claimed is:

1. A formulation which comprises an anti-HLA-DR antibody molecule coupled to a liposome, said antibody molecule being selected from the group consisting of a whole antibody and an antigen binding fragment thereof, said formulation capable of binding to an HLA-DR protein present at both the surface of an infectious agent and at the membrane surface of a cell, wherein said liposome comprises a mixture of dipalmitoylphosphatidylcholine:dipalmitoylphosphatidylglycerol:dipalmitoylphosphatidylethanolamine-polyethyleneglycol in a molar ratio of 10:3:0.33 or dipalmitoylphosphatidylcholine:dipalmitoylphosphatidylglycerol:distearoylphosphatidylethanolamine-polyethyleneglycol in a molar ratio of 10:3:0.83.

2. The formulation according to claim 1, further comprising an additional antibody molecule to one or more proteins selected from the group consisting of a histocompatibility complex protein, a membrane ATPase, thy-1, an interleukin receptor, annexin II, CD3 (T3), CD4 (T4), CD5 (Ti), CD6 (T12), CD8 (T8), CD11a (LFA-1), CD11b (Mac-1), CD11c (gp150,95), CD1 (Lewis X), CD18, CD19, CD25 (Tac), CD30 (Ki-1), CD43 (leukosialin, sialophorin), CD44 (Pgp-1), CD48 (Blast-1), CD54 (ICAM-1), CD55 (DAF), CD59

(protectin, Mac inhibitor), CD63, CD71 (transferrin receptor), CDw108 (GR2), cyclophilin A, cytoskeletal proteins and β 2-microglobulin.

3. The formulation according to claim 1, which further comprises a drug encapsulated within the liposome, said drug effective against a disease or against the symptoms of a disease caused by said infectious agent.

4. The formulation according to claim 1, wherein said HLA-DR protein is present at the membrane surface of a lymphoid cell or a cell of the reticuloendothelial system.

5. The formulation according to claim 3, wherein said HLA-DR protein is present at the membrane surface of a lymphoid cell or a cell of the reticuloendothelial system.

6. The formulation according to claim 4, wherein said HLA-DR protein is acquired by HIV.

7. The formulation according to claim 5, wherein said HLA-DR protein is acquired by HIV.

8. The formulation according to claim 4, further comprising an additional antibody molecule to one or more of CD4, MHC-I and CD54 proteins.

9. The formulation according to claim 5, further comprising an additional antibody molecule to one or more of CD4, MHC-I and CD54 proteins.

10. The formulation according to claim 3, wherein said drug is selected from AZT, ddI, ddC, 3TC, indinavir, saquinavir, ritonavir, nelfinavir, ganciclovir, foscarnet, ribavirin, amphotericin B and nystatin A.

11. The formulation according to claim 1, wherein said antibody molecule is an anti-Fab' antibody fragment directed against a HLA-DR protein.

12. The formulation according to claim 1, wherein said infectious agent is HIV.

13. The formulation according to claim 2, which further comprises a drug encapsulated within the liposome, said drug effective against a disease or against symptoms of a disease caused by said infectious agent.

14. The formulation according to claim 13, wherein said drug is selected from AZT, ddI, ddC, 3TC, indinavir, saquinavir, ritonavir, nelfinavir, ganciclovir, foscarnet, ribavirin, amphotericin B and nystatin A.

15. A formulation which comprises an anti HLA-DR antibody molecule coupled to a liposome, said antibody molecule being selected from the group consisting of a whole antibody and an antigen binding fragment thereof, and the liposome containing a drug, said formulation capable of binding to an HLA-DR protein present at both the surface of an infectious agent and at the membrane surface of a cell and of delivering said drug to said cell and infectious agent, wherein said liposome comprises a mixture of dipalmitoylphosphatidylcholine:dipalmitoylphosphatidylglycerol:dipalmitoylphosphatidylethanolamine-polyethyleneglycol in a molar ratio of 10:3:0.33 or dipalmitoylphosphatidylcholine:dipalmitoylphosphatidylglycerol:distearoylphosphatidylethanolamine-polyethyleneglycol in a molar ratio of 10:3:0.83.

16. The formulation of claim 15, wherein said infectious agent is HIV.

\* \* \* \* \*